(12) United States Patent
Broliden et al.

(10) Patent No.: US 6,818,612 B2
(45) Date of Patent: Nov. 16, 2004

(54) USE OF PARVOVIRUS CAPSID PARTICLES IN THE INHIBITION OF CELL PROLIFERATION AND MIGRATION

(76) Inventors: Kristina Broliden, Skogsviksvägen 51, S-182 39 Danderyd (SE); Magnus Westgren, Skillinggränd 5, S-112 20 Stockholm (SE)

(*) Notice: Subject to any disclaimer, the term of this patent is extended or adjusted under 35 U.S.C. 154(b) by 35 days.

(21) Appl. No.: 09/991,433

(22) Filed: Nov. 16, 2001

(65) Prior Publication Data

US 2003/0017596 A1 Jan. 23, 2003

Related U.S. Application Data

(63) Continuation-in-part of application No. 09/447,693, filed on Nov. 23, 1999, now abandoned.

(30) Foreign Application Priority Data

Nov. 24, 1998 (SE) ............................................. 9804022

(51) Int. Cl.[7] ........................ A61K 38/00; A61K 38/04; A61K 38/08; A61K 38/10; C12N 7/04

(52) U.S. Cl. ......................... 514/2; 530/326; 530/327; 530/328; 530/329; 530/330; 530/350; 435/235.1; 435/236

(58) Field of Search ............................... 514/2, 12, 18, 514/21; 435/4, 5, 7.2, 69.1, 71.1, 456, 235.1; 530/300, 328, 326, 327, 329, 330, 331, 350; 424/93.6, 184.1, 185.1, 186.1, 193.1, 196.11, 233.1

(56) References Cited

U.S. PATENT DOCUMENTS

| | | | |
|---|---|---|---|
| 4,612,337 A | 9/1986 | Fox, Jr. et al. | 523/113 |
| 4,818,540 A | 4/1989 | Chien et al. | 424/448 |
| 4,908,773 A | 3/1990 | Pantoliano et al. | 364/495 |
| 5,288,707 A | 2/1994 | Metternich | 514/19 |
| 5,508,186 A | 4/1996 | Young et al. | 435/235 |
| 5,552,534 A | 9/1996 | Hirschmann et al. | 538/17.4 |
| 5,811,515 A | 9/1998 | Grubbs et al. | 530/330 |
| 5,817,626 A | 10/1998 | Findeis et al. | 514/12 |
| 5,817,879 A | 10/1998 | Hirschmann et al. | 568/333 |
| 5,821,231 A | 10/1998 | Arrhenius et al. | 514/18 |
| 5,827,647 A | 10/1998 | Young et al. | |
| 5,874,529 A | 2/1999 | Gilon et al. | 530/317 |
| 5,916,563 A | 6/1999 | Young et al. | |
| 6,001,371 A | 12/1999 | Young et al. | |
| 6,132,732 A | 10/2000 | Young et al. | |
| 6,204,044 B1 | 3/2001 | Brown | |
| 6,274,307 B1 | 8/2001 | Soutschek et al. | |

FOREIGN PATENT DOCUMENTS

| | | |
|---|---|---|
| EP | 0 491 824 B1 | 5/1995 |
| WO | WO 91/04330 A | 4/1991 |
| WO | WO 91/12269 A1 | 8/1991 |

OTHER PUBLICATIONS

Gharakanian et al., Journal of General Virology, vol. 84, pp. 2111–2116 (2003).*
Jean et al., Applied and Environmental Microbiology, vol. 67, No. 12., pp. 5593–5600 (2001).*
Bowie et al., Science, vol. 247 No. 4948, pp. 1306–1310 (1990).*
Bork et al., Genome Research, vol. 10, pp. 398–400 (2000).*
Anderson and Young, Monographs in Virology, 20 (1997).
Armitage, "Emerging Application of Recombinant Human . . . ," Blood, vol. 92, No. 12, pp. 4491–4508 (Dec. 15, 1998).
Benet, et al., "Pharmacokinetics: The Dynamics of Drug Absorption, Distribution, and Elimination," The Pharmacological Basis of Therapeutics, 8th Ed., Goodman and Gilman's, pp. 3–32 (1990).
Bostic, et al., J. Infect. Dis., 179:619 (1999).
Brown, et al., J. Virol., 65:2702 (1991).
Brown, et al., Science, 262:114 (1993).
Burgess, et al., "Possible Dissociation of the Heparin–binding and Mltogenic Activities of . . . ," The Journal of Cell Biology, vol. 111, pp. 2129–2138 (11/90).
Chipman, et al., "Cryo–electron microscopy studies of ampty capsids of human parvovirus B19 . . . ," Proc. Natl. Acad. Sci. USA, vol. 93, pp. 7502–7506 (07/96).
Cotmore, et al., Science, 226:1161 (1984).
Ek, et al., "Colony Formation of Human Fetal CD34+ Hematopoietic Cells," Fetal Diagn. Ther., 11:326–334, 1996.
Ek, et al., "Cytokine Stimulation of Human Fetal Hematopoietic Cells," Fetal Diagn. Ther. 11:318–325, 1996.
Ek, et al., "Effects of cryopreservation on subsets of fetal liver cells," Bone Marrow Transplantation, 11:395–398, 1993.
Ek, et al., "Immunological capacity of human fetal liver cells," Bone Marrow Transplantation, 14:9–14, 1994.
Erdman, et al., J. Gen. Virol., 77:2767 (1996).

(List continued on next page.)

Primary Examiner—James Housel
Assistant Examiner—Zachariah Lucas
(74) Attorney, Agent, or Firm—Knobbe, Martens, Olson & Bear

(57) ABSTRACT

The invention described herein relates to the discovery of methods and compositions for the inhibition of growth and/or migration of cells that have a receptor that interacts with a parvovirus B19 capsid or fragment thereof (e.g., a P antigen containing cell), including but not limited to, cells of hematopoietic origin and endothelial cells. More specifically, parvovirus capsid particles or fragments of parvovirus capsid proteins are used to manufacture medicaments that can be administered to a subject to inhibit hematopoietic progenitor cell growth (e.g., prior to stem cell transplantation), endothelial cell growth, (e.g., as an anti-tumorigenesis treatment or to prevent restenosis or fibrotic build up following prosthetic implantation), or to prevent disorders that involve the abnormal proliferation of cells that have the P antigen (e.g., Polycythemia Vera).

29 Claims, 20 Drawing Sheets-

OTHER PUBLICATIONS

Figure 1A:
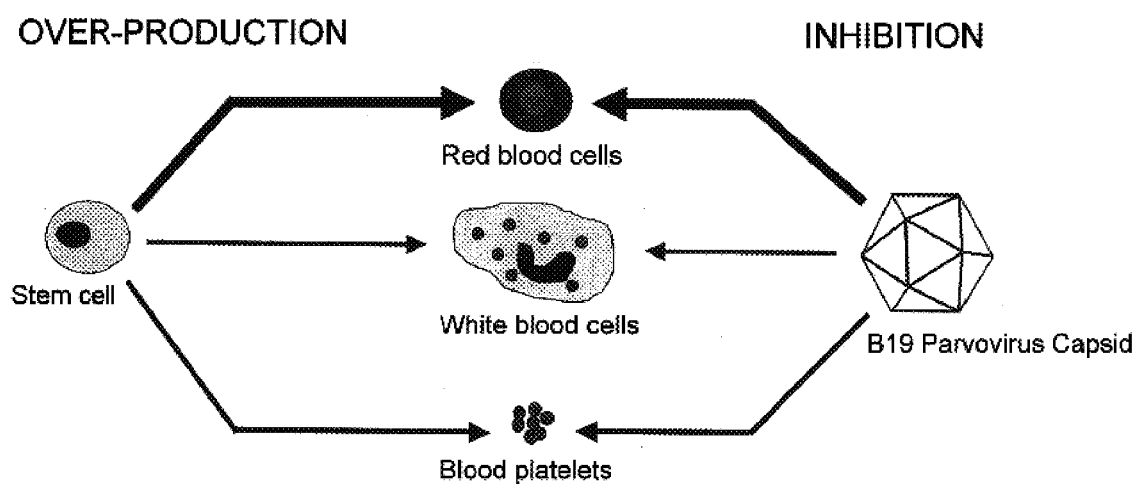
Figure 1B:
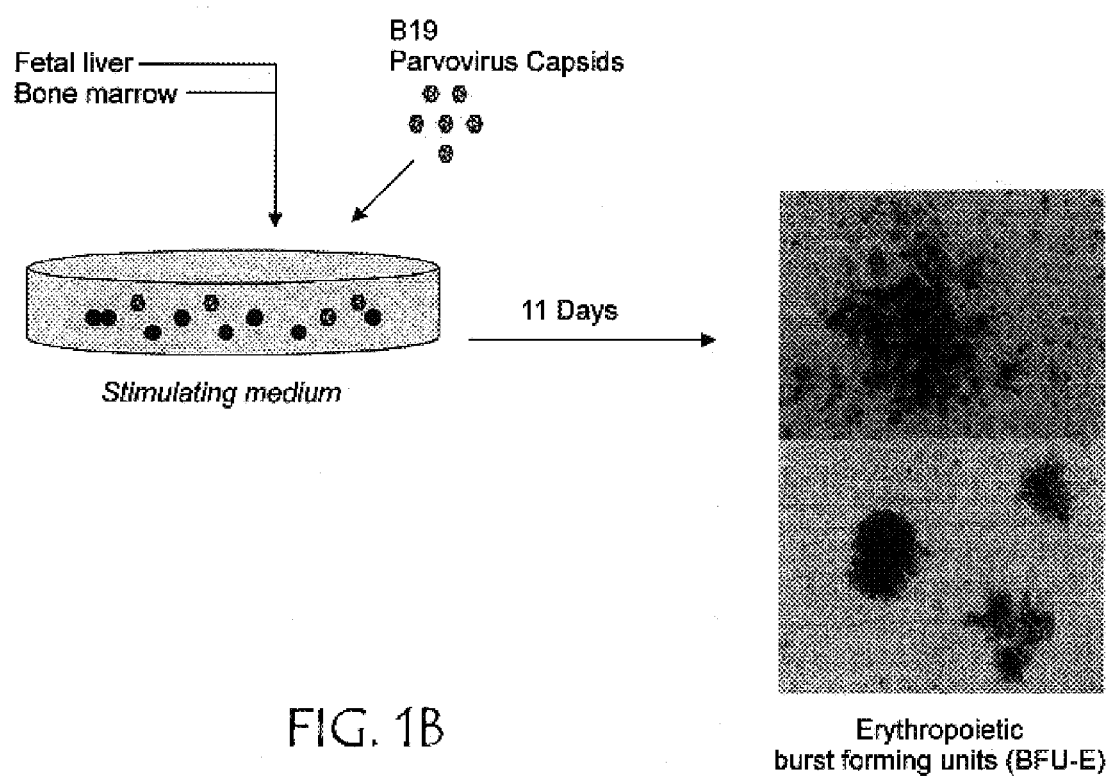
Figure 1C:
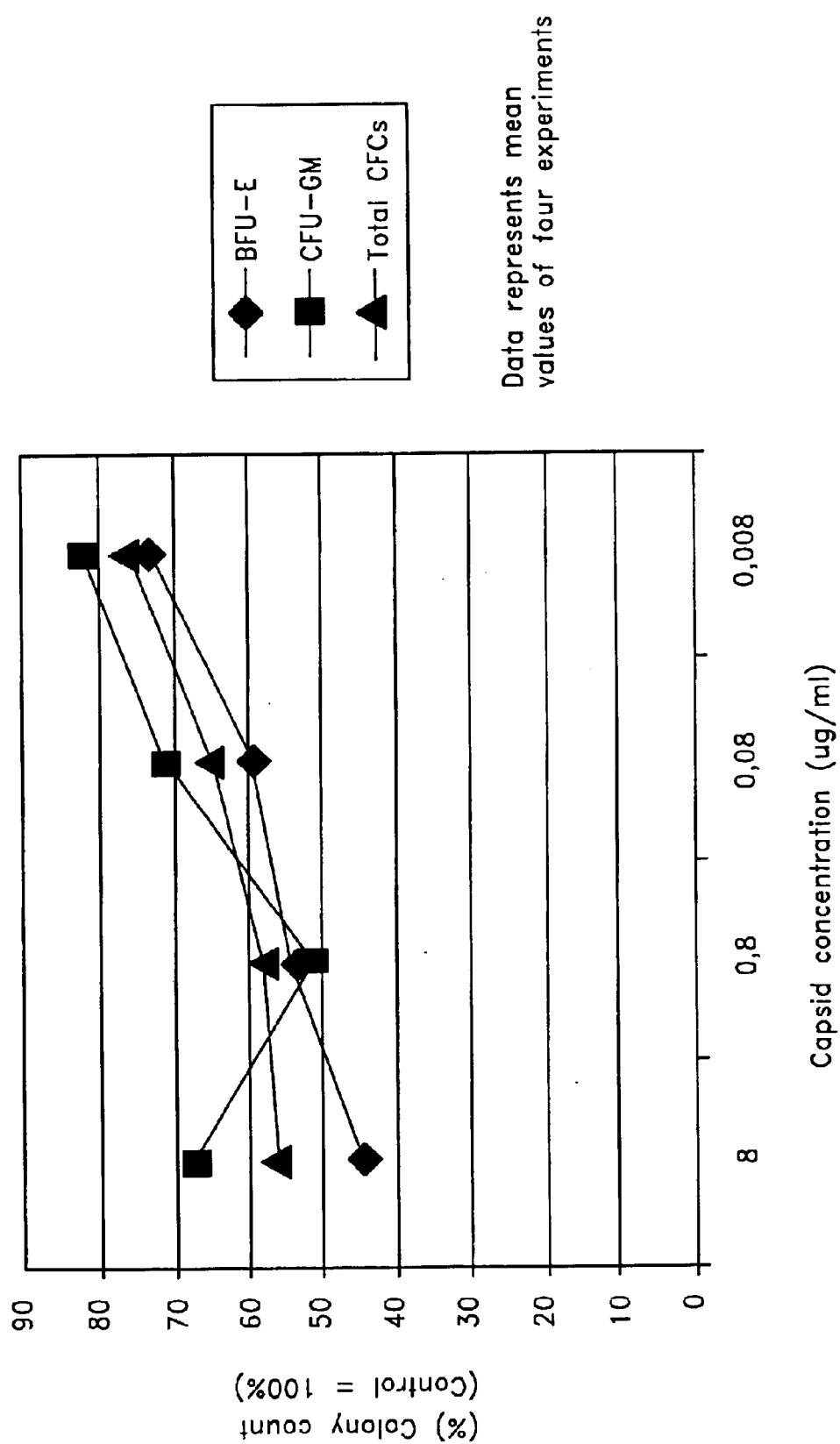

Farmer, et al., in TIPS, 9/82, pp. 362–365.
Fields, et al., *Virology, vol. 2, 3rd edition*, Lippincott–Raven Pub., Philadelphia, PA, p. 2202, 2204, 2207 (1996).
Giralt, et al., *Blood*, 89:4531 (1997).
Jain, "Vascular and interstitial barriers to delivery of therapeutic agents in tumors," *Cancer Metaslasis Rev.* 9(3):253–266, Nov. 1990.
Jain, "Delivery of Molecular Medicine to Solid Tumors," *Science*, vol. 271, pp. 1079–1080, Feb. 23, 1996.
Kajigaya, et al., *Proc. Natl. Acad. Sci. USA*, 86:7601 (1989).
Kajigaya, et al., *Proc. Natl. Acad. Sci. USA*, 88:4646 (1991).
Kaltenbronn, et al., *J. Med. Chem.*, 33:838–845 (1990).
Kemp, D.S., Tibech, "Peptidomimetics and the Template Approach to nucleation of beta–sheets and alpha–helices in Peptides", vol. 8, pp. 249–255 (1990).
Lazar, et al., *Molecular and Cellular Biology*, 8(3):1247–1252, Mar. 1988.
Le Blanc, et al., *European Journal of Haematology* 53:145–149, 1994.
Lindton, et al., "Mixed Lymphocyte Culture of Human Fetal Liver Cells," *Fetal Diagn. Ther.*, 15:71–78, 2000.
Lindton, et al., "Recombinant Parvovirus B19 Empty Capsids Inhibit Fetal Hematopoietic Colony Formation in vitro," *Fetal Diagn. Ther.*, 16:26–31, 2001.
Liu, et al., "Interleukin–6 and the Granulocyte Colony–Stimulating Factor Receptor Are Major Independent Regulators . . . ," *Blood*, vol. 90, No. 7, pp. 2583–2590, Oct. 1, 1997.

Morey and Flemming, *Br. J. Hematol.*, 82:302 (1992).
Mortimer, et al., *Nature*, 302:426–429 (1983).
Ozawa, et al., *J. Virol.*, 62:2884 (1988).
Pabo, C.O., et al., *Biochemistry*, 25:5987–5991 (1986).
Perry, L.J. & Wetzel, R., Science, 226:555–557 (1984).
Rosenfeld, et al., *The Journal of Clinical Investigation*, 89:2023–2029, Jun. 1992.
Shields, et al., "In Vitro Hematopoiesis is Inhibited in Humans and non–human Primates by Recombinant Parvo Virus Capsid," 20th Annual Meeting of the Society for Maternal–Fetal Medicine, American Journal of Obstetrics and Gynecology, vol. 181, No. 1, part 2, Jan. 2002.
Slavin, et al., *Blood*, 91:756 (1998).
Verber, et al., in TINS, 9/85, pp. 392–396.
von dem Borne, et al., *Br. J. Hematol.*, 63:35–46 (1986).
Westgren, et al., *Am. J. Obstet. Gynecol.*, 176:49 (1996).
Shade, et al., "Nucleotide Sequence and Genome Organization of Human Parvovirus B19 Isolated from the Serum of a Child during Aplastic Crises," *Journal of Virology*, pp. 921–936, Jun. 1986.
Anderson and Young, editors, "Human Parvovirus B19," *Monographs in Virology*, vol. 20, 1997.

* cited by examiner

FIG. 4

FIG. 6

Neutralization of 8.3.2000 VP2 using MAB 8292 (Chemicon)
Four cultures, two donors Legend:
- 8.3.2000 VP2 #2
- MAB 8292 #2
- 8.3.2000 VP2 #1
- MAB 8292 #1

X-axis: MAB Conc in 11 days culture (ug/mL)
Y-axis: Colony count (Relative medium control)

VP2 at 1.9 ug/mL without MAB

VP2 (batch 8.3.2000)
Cleaved by three different endoproteases (LYS, ARG and GLU)

FIG. 7A  VP2 CLEAVAGE-LYS
FIG. 7B  VP2 CLEAVAGE-ARG
FIG. 7C  VP2 CLEAVAGE-GLU

VP2 PEPTIDEPOOLS 1 – 2

VP2 PEPTIDEPOOLS 3 – 4

VP2 PEPTIDEPOOLS 5 – 6

VP2 PEPTIDEPOOLS 7 – 8

USE OF PARVOVIRUS CAPSID PARTICLES IN THE INHIBITION OF CELL PROLIFERATION AND MIGRATION

CROSS-REFERENCE TO RELATED APPLICATIONS

This application is a continuation-in-part of U.S. Ser. No. 09/447,693, filed Nov. 23, 1999, now abandoned, which claims priority to Swedish Patent Application No. 9804022-3, filed Nov. 24, 1998, both of which are hereby expressly incorporated by reference in their entireties.

FIELD OF THE INVENTION

The present invention relates to the discovery of methods and compositions for the inhibition of cell growth and migration. More specifically, B19 parvovirus capsids or fragments of B19 parvovirus capsid proteins are incorporated into medicaments that can be administered to a subject to inhibit the growth and/or migration of cells that have a receptor that interacts with a parvovirus B19 capsid or fragment thereof (e.g., a P antigen containing cell), including, but not limited to, cells of hematopoietic origin and endothelial cells.

BACKGROUND OF THE INVENTION

The B19 parvovirus is a human pathogen that can be associated with various clinical conditions, ranging from mild symptoms (erythema infectiosum) to more serious diseases in persons who are immunocompromised or suffer from hemolytic anemias. Hydrops fetalis and intrauterine fetal death are well-known complications of B19 parvovirus infection during pregnancy. (Anderson and Young, *Monographs in Virology*, 20 (1997)). The B19 parvovirus particles have icosohedral symmetry, a diameter of 18 to 26 nm, and are composed of 60 capsid proteins, approximately 95% of which are major capsid proteins (VP2) that have a molecular weight of 58 kd. (Fields et al., *Virology vol.* 2, 3rd edition, Lipponcott-Raven Publishers, Philidelphia, Pa., p. 2202 (1996)). Approximately, 3–5% of the capsid proteins that compose a B19 parvovirus capsid are called minor capsid proteins (VP1), which have a molecular weight of 83 kd, and differ from VP2 by an additional 227 amino acids at the amino terminus. (Id.).

The B19 parvovirus is extraordinarily tropic for human erythroid cells and cultures of bone marrow. B19 parvovirus binds to human erythroid progenitor cells, for example, and inhibits hematopoietic colony formation by replicating in these cells. (Brown et al., *Science*, 262:114 (1993) and Mortimer et al., *Nature*, 302:426 (1983)). The suppression of hematopoietic cells has also been seen in bone marrow samples from infected individuals, resulting in transient anemia and, in rare case, transient pancytopenia. (Saunders et al., *Br J Haematol*, 63:407 (1986)). Further, B19 parvovirus is known to cause bone marrow suppression in natural and experimental human infections. (Anderson and Young, *Monographs in Virology*, 20 (1997)).

The cellular receptor for B19 parvovirus has been identified as globoside or erythrocyte P antigen, a textrahexoceramide. (Fields et al., *Virology vol.* 2, 3rd edition, Lipponcott-Raven Publishers, Philidelphia, Pa., p. 2204 (1996)). The P antigen is found on mature erythrocytes, erythroid progenitors, megakaryocytes, endothelium, kidney cortex, placenta, fetal myocardium (von dem Borne et al., *Br J Hematol*, 63:35 (1986)) and pronormoblasts from fetal liver. (Morey and Flemming, *Br J Haematol*, 82:302 (1992)). Individuals who genetically lack the P antigen are not susceptible to B19 parvovirus infection and administration of either excess P antigen or monoclonal antibodies directed to the P antigen can protect erythroid progenitors from infection with B19 parvovirus. (Id.).

Additionally, neutralizing antibodies that recognize several regions of the B19 parvovirus particle have been generated. For example, monoclonal antibodies directed to epitopes of VP2, such as found at amino acids 38–87, 253–272, 309–330, 328–344, 359–382, 449–468, and 491–515, and the unique region of VP1 can neutralize B19 parvovirus. (Fields et al., *Virology vol.* 2, 3rd edition, Lipponcott-Raven Publishers, Philidelphia, Pa., p. 2207 (1996)).

Genetically engineered expression systems for the production of B19 parvovirus antigens have also been developed. (Kajigaya et al., *Proc Natl Acad Sci USA,* 86:7601 (1989); Kajigaya et al., *Proc Natl Acad Sci USA,* 88:4646 (1991); Brown et al., *J Virol,* 65:2702 (1991)). Like the native particles, recombinant B19 parvovirus capsids, produced in a baculovirus system, are composed of both VP1 and VP2 and these capsid proteins self assemble to form virus-like particles (VLPs). (Kajigaya et al., *Proc Natl Acad Sci USA,* 88:4646 (1991)). Electron microscopic analyses of the B19 parvovirus capsids revealed that the VLPs are structurally similar to plasma-derived virions. (Kajigaya et al., *Proc Natl Acad Sci USA,* 88:4646 (1991)). B19 parvovirus VLPs are currently being evaluated as a potential vaccine against B19 parvovirus infection and preliminary results show a good neutralizing response without severe side effects. (Bostic et al, *J. Infect. Dis.,* 179:619 (1999). While many are trying to prevent B19 parvovirus infection by administering B19 parvovirus capsids, none have sought to exploit the properties of the B19 parvovirus capsid, B19 parvovirus capsid proteins, or fragments thereof to develop novel medicaments that inhibit cell proliferation or migration.

BRIEF SUMMARY OF THE INVENTION

It has been discovered that the B19 parvovirus capsid, B19 parvovirus capsid proteins, or fragments thereof inhibit the growth and/or migration of cells that have a receptor that interacts with a parvovirus B19 capsid or fragment thereof (e.g., a P antigen containing cell). The data presented herein demonstrate that the B19 parvovirus capsid, B19 parvovirus capsid proteins, and fragments thereof, inhibit hematopoiesis and endothelial cell growth and migration. Accordingly, the compositions described herein can be used to reduce the production of red blood cells, white blood cells, and blood platelets, as well as, inhibit the growth and migration of other cells having a receptor that interacts with a parvovirus B19 capsid or fragment thereof (e.g., a P antigen containing cell), such as endothelial cells. Because many diseases or maladies are associated with an overproduction of cells of hematopoietic origin and/or invasive growth or migration of cells of endothelial origin, the compositions and methods described herein have significant therapeutic and prophylactic utility.

Embodiments of the invention include medicaments comprising, consisting essentially of, or consisting of B19 parvovirus capsid, B19 parvovirus capsid proteins, or fragments thereof, preferably the tripeptide (QQY) and a 10-mer peptide (NKGTQQYTDQ SEQ. ID. NO. 5), which can be administered to subjects in need of an agent that inhibits cell growth and/or migration. The B19 parvovirus capsid proteins and fragments thereof, preferably VP2 capsid proteins and fragments thereof, can be prepared synthetically, using peptide chemistry or genetic engineering, or can be made by cleaving B19 parvovirus capsids, desirably VP2 capsids, with various proteases, for example an endoprotease, which cleaves at a lysine or arginine residue.

The methods of the invention include approaches to manufacture medicaments that can be used to inhibit the growth or migration of cells that have a receptor that interacts with a parvovirus B19 capsid or fragment thereof (e.g., a P antigen containing cell). By one approach, for example, an active ingredient consisting of, consisting essentially of, or comprising empty, noninfectious, recombinant B19 parvovirus capsids, B19 parvovirus capsid proteins, or fragments of B19 parvovirus capsid proteins, preferably the tripeptide (QQY) and a 10-mer peptide (NKGTQQYTDQ SEQ. ID. NO. 5), are incorporated into a medicament with or without a pharmaceutically acceptable carrier or support. The amount of active ingredient can be varied depending on the potency of the inhibition needed and the length of treatment period desired from a single dose.

The medicaments described herein are preferably used to inhibit hematopoietic cell growth, endothelial cell growth, or endothelial cell migration. The medicaments described herein are used, for example, to treat hematological proliferative disorders, angiogenesis, tumorigenesis, or endothelial cell ingrowth into an implanted prosthetic device. Further, the medicaments described herein can be provided to a subject, including a fetus, prior to stem cell transplantation. Accordingly, methods of prevention and/or treatment of diseases or conditions associated with hematopoietic or endothelial cell proliferation or migration are aspects of the invention and many of the embodied methods are characterized in that they involve providing a subject at risk of having such a disease or a subject that is afflicted with such a disease with a therapeutically effective amount of a B19 parvovirus capsid, B19 parvovirus capsid proteins, preferably VP2 capsid proteins, or fragments thereof, preferably the tripeptide (QQY) and a 10-mer peptide (NKGTQQYTDQ SEQ. ID. NO. 5).

In other embodiments, methods to prevent or treat Polycytemia Vera are provided, wherein a subject at risk for Polycytemia Vera or a subject afflicted with Polycytemia Vera is identified and said subject is provided a therapeutically effective amount of a capsid agent selected from the group consisting of B19 parvovirus capsid, B19 parvovirus capsid proteins, preferably VP2 capsid proteins, and fragments thereof, preferably the tripeptide (QQY) and a 10-mer peptide (NKGTQQYTDQ SEQ. ID. NO. 5). The capsid agents, described above, can be provided to said subject neat or as part of a medicament containing other materials including, but not limited to, pharmaceutically acceptable supports or carriers. In a similar fashion, other hematopoietic proliferative disorders can be treated or prevented. That is, a subject in need of a capsid agent that inhibits a hematopoietic proliferative disorder is identified and said subject is provided an effective amount of capsid agent selected from the group consisting of B19 parvovirus capsid, B19 parvovirus capsid proteins, preferably VP2 capsid proteins, and fragments thereof, preferably the tripeptide (QQY) and a 10-mer peptide (NKGTQQYTDQ SEQ. ID. NO. 5). In some embodiments, the progress or effectiveness of treatment is monitored or measured (e.g., analysis of red blood cell hematocrit).

A method of treating a subject prior to stem cell transplantation is also provided, wherein a subject in need of stem cell transplantation is identified and said subject is provided an effective amount of capsid agent selected from the group consisting of B19 parvovirus capsid, B19 parvovirus capsid proteins, preferably VP2 capsid proteins, and fragments thereof, preferably the tripeptide (QQY) and a 10-mer peptide (NKGTQQYTDQ SEQ. ID. NO. 5).

In more embodiments, methods of inhibiting the growth or migration of a cell having a receptor that interacts with a parvovirus B19 capsid or fragment thereof (e.g., a P antigen containing cell) are provided. By one approach, for example, a cell is contacted with a capsid agent selected from the group consisting of B19 parvovirus capsid, B19 parvovirus capsid proteins, preferably VP2 capsid proteins, and fragments thereof, preferably the tripeptide (QQY) and a 10-mer peptide (NKGTQQYTDQ SEQ. ID. NO. 5), and the inhibition of cell growth or cell migration is monitored or measured. In some embodiments, the cell is of hematopoietic origin or an endothelial cell.

Methods of inhibiting tissue ingrowth into an implanted prosthesis are also provided. These approaches involve identifying a subject in need of a capsid agent that inhibits tissue ingrowth into an implanted prosthesis and providing said subject an effective amount of capsid agent selected from the group consisting of B19 parvovirus capsid, B19 parvovirus capsid proteins, preferably VP2 capsid proteins, or fragments thereof, preferably the tripeptide (QQY) and a 10-mer peptide (NKGTQQYTDQ SEQ. ID. NO. 5). Approaches to manufacture ingrowth inhibiting implantable prosthesis are also provided, wherein a capsid agent selected from the group consisting of a B19 parvovirus capsid, B19 parvovirus capsid proteins, preferably VP2 capsid proteins, and fragments thereof, preferably the tripeptide (QQY) and a 10-mer peptide (NKGTQQYTDQ SEQ. ID. NO. 5) is joined to said implantable prosthesis. Embodiments also include implantable prosthesis, e.g., stents, valves, artificial joints, having said capsid agents.

More embodiments involve methods of treating or preventing tumorigenesis, wherein a subject in need of a capsid agent that inhibits hematopoietic and/or endothelial cell growth is identified and said subject is provided an effective amount of capsid agent selected from the group consisting of B19 parvovirus capsid, B19 parvovirus capsid proteins, preferably VP2 capsid proteins, and fragments thereof, preferably the tripeptide (QQY) and a 10-mer peptide (NKGTQQYTDQ SEQ. ID. NO. 5).

Still more embodiments concern kits having a capsid agent selected from the group consisting B19 parvovirus capsid, B19 parvovirus capsid proteins, preferably VP2 capsid proteins, and fragments thereof, preferably the tripeptide (QQY) and a 10-mer peptide (NKGTQQYTDQ SEQ. ID. NO. 5), and instructions for dosage and administration to a subject for hematopoietic progenitor cell growth inhibition, hematopoietic progenitor cell growth inhibition, endothelial cell growth inhibition or treatment of a hematological proliferative disease. These kits may also have a device to remove blood from a subject and/or a devices to measure blood hematocrit or endothelial cell growth.

BRIEF DESCRIPTION OF THE DRAWINGS

FIG. 1A This figure illustrates the use of parvovirus capsids to inhibit hematopoiesis so as to prevent the overproduction of red blood cells, white blood cells, and blood platelets.

FIG. 1B This figure illustrates the general methodology employed in the colony formation assays described herein.

FIG. 1C This figure shows a graphical representation of the results of colony formation assays performed on cells from human cord blood that were contacted with varying concentrations of B19 parvovirus capsids (VP1/2).

Figure 2:
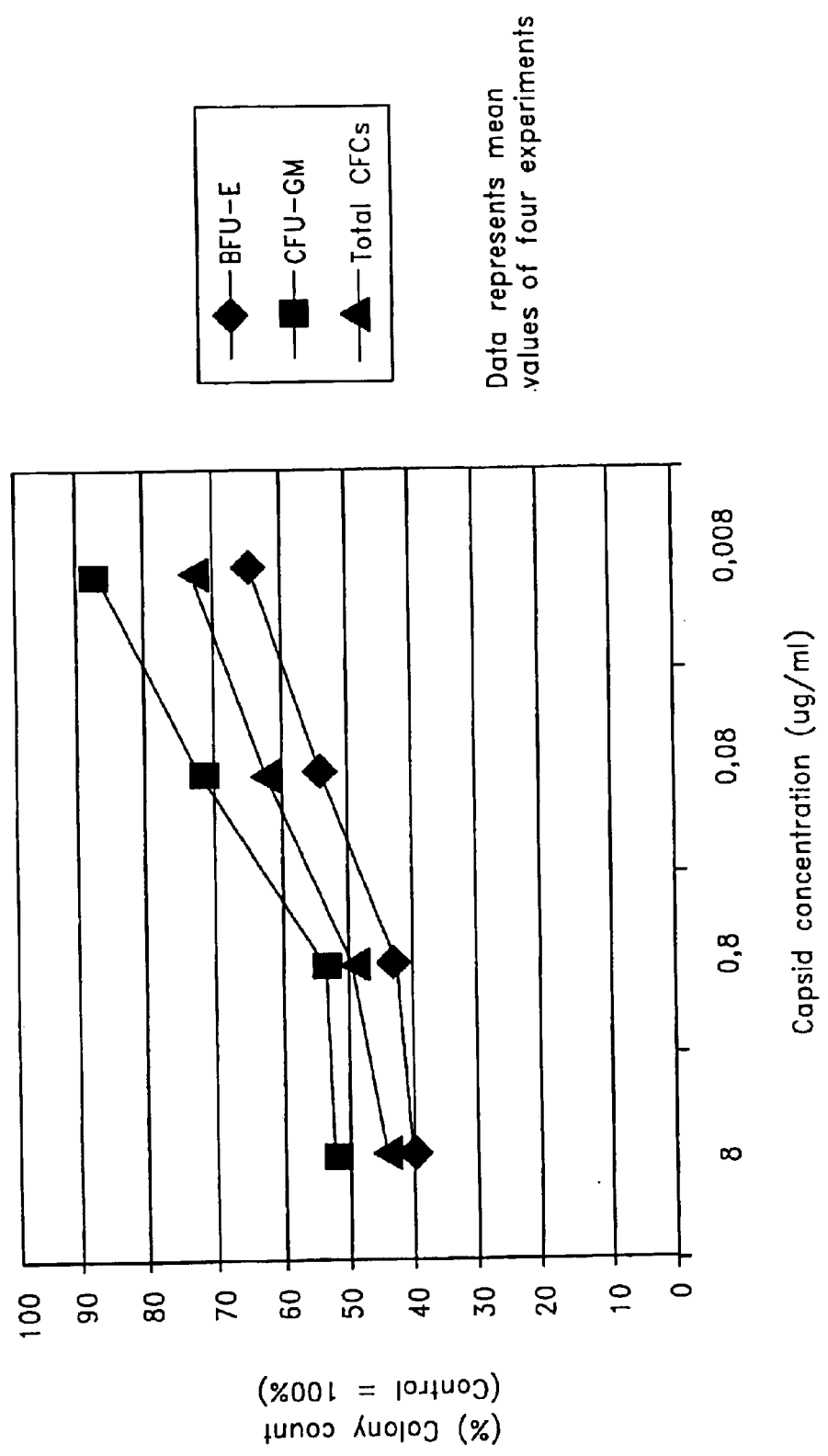

FIG. 2 This figure shows a graphical representation of the results of colony formation assays performed on cells from monkey (Baboon and Macaque) bone marrow that were contacted with varying concentrations of B19 parvovirus capsids (VP1/2).

Figure 3:
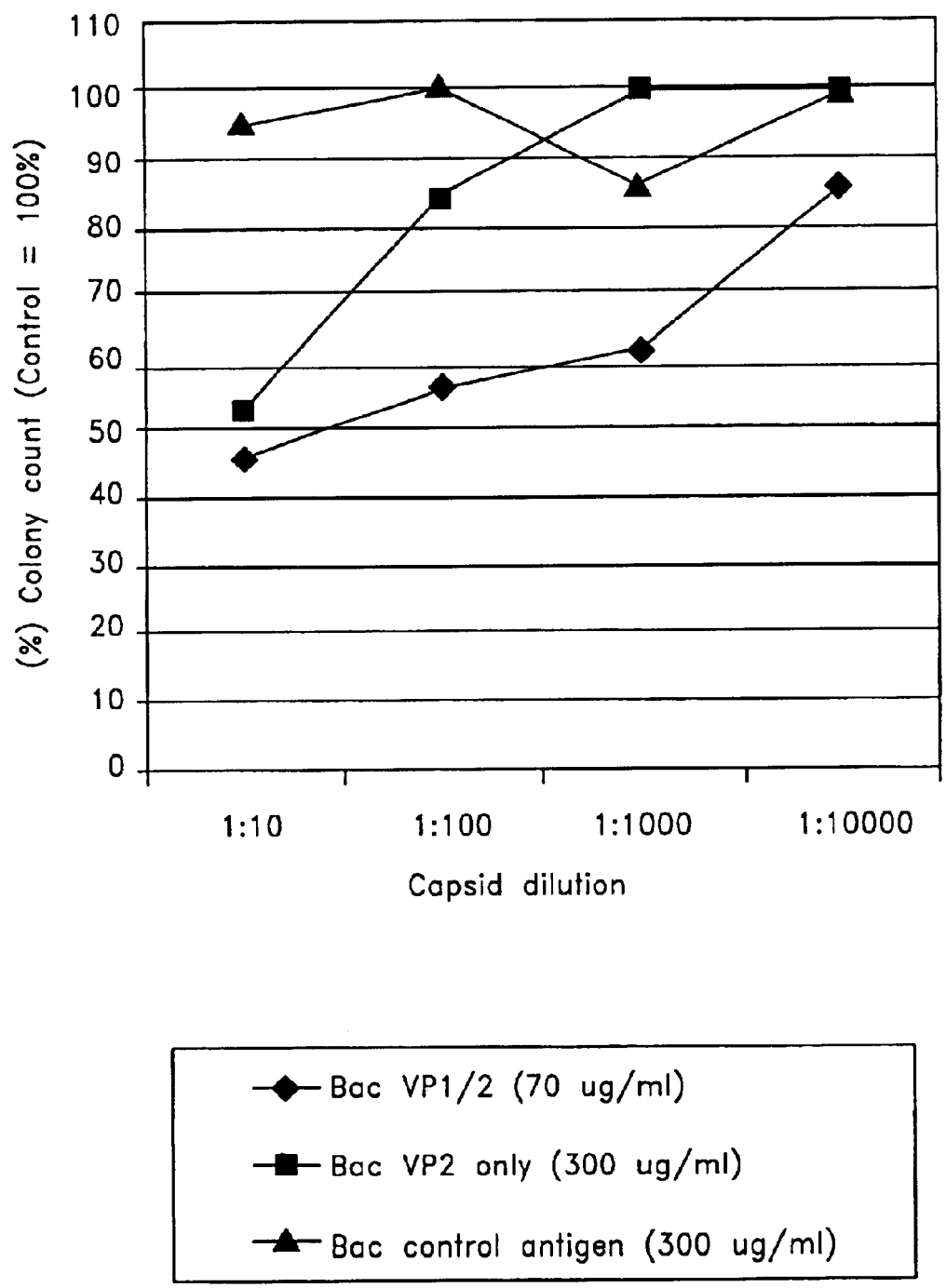

FIG. 3 This figure shows a graphical representation of the results of colony formation assays performed on cells from human fetal liver that were contacted with varying concentrations of B19 parvovirus capsids (BacVP1/2), B19 parvovirus capsids having only VP2 (Bac VP2 only), or a control antigen (Bac control antigen).

Figure 4:
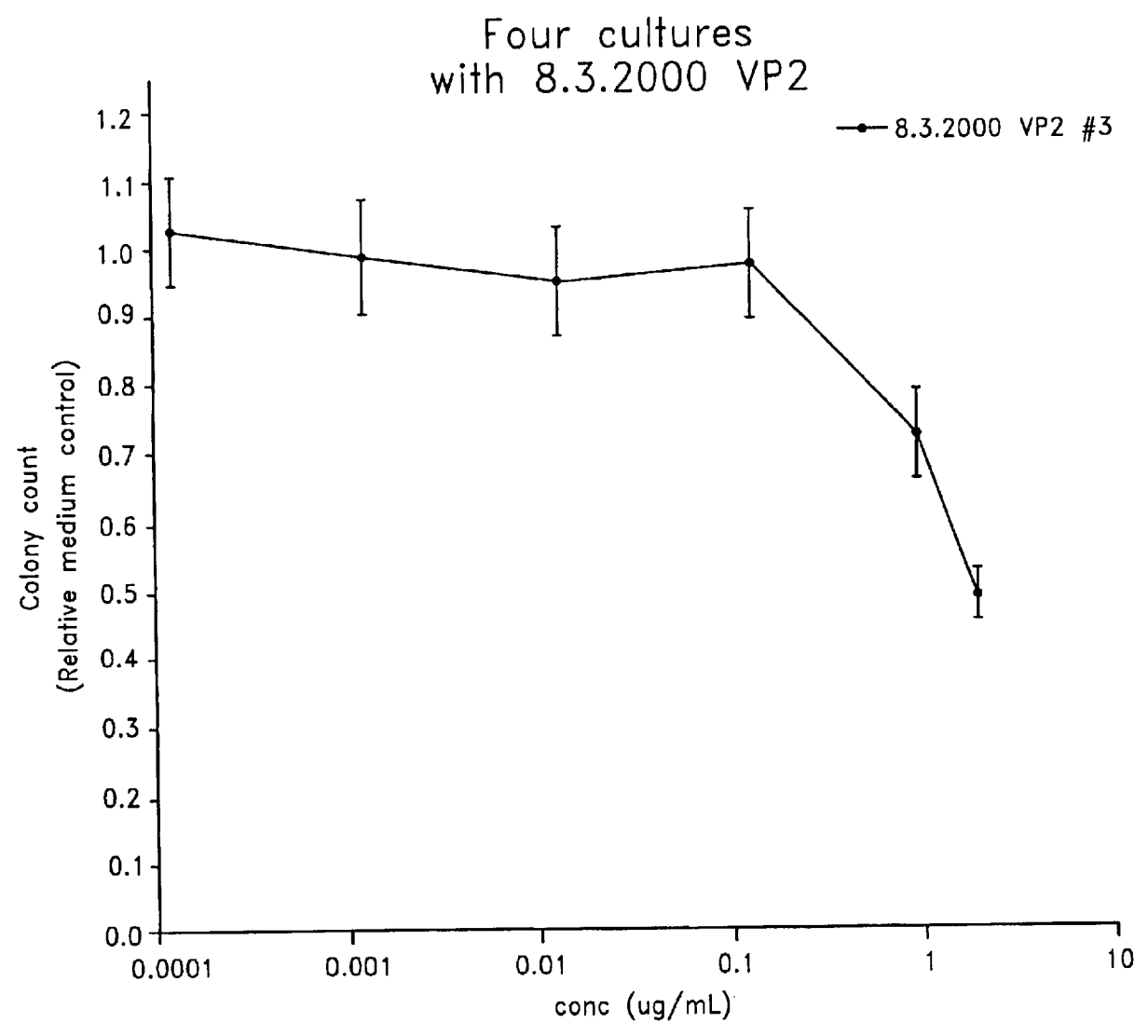

FIG. 4 This figure shows a graphical representation of the results of colony formation assays performed on cells from fetal liver that were contacted with varying concentrations of B19 parvovirus VP2 capsids.

Figure 5:
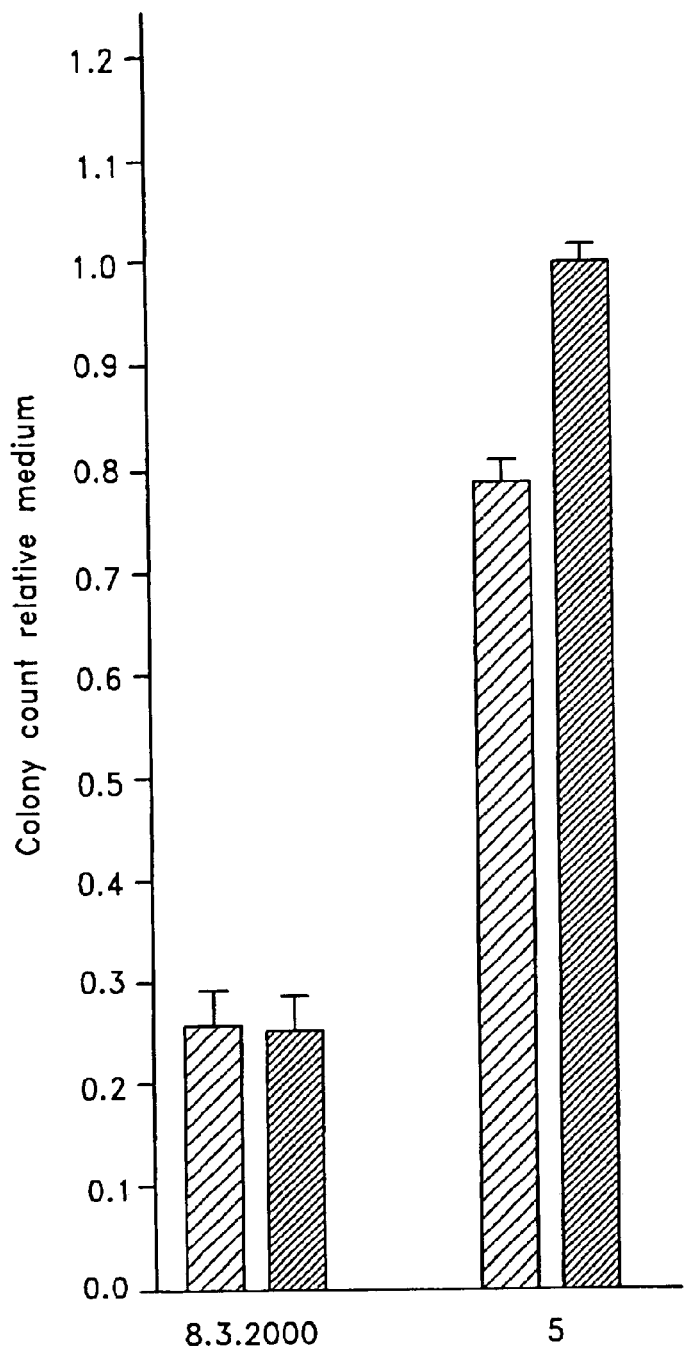

FIG. 5 This figure shows a graphical representation of the results of colony formation assays performed on fetal liver cells that were contacted with varying concentrations of B19 parvovirus VP2 capsids (denoted 8.3.2000) and CPV VP2 capsids (denoted 5).

FIG. 6 This figure shows a graphical representation of the results of colony formation assays performed on fetal liver cells that were contacted with B19 parvovirus VP2 capsids that had been incubated with different dilutions of anti-B19 parvovirus monoclonal antibody.

FIG. 7A This figure shows a graphical representation of the results of colony formation assays performed on fetal liver cells that were contacted with intact B19 parvovirus VP2 capsids or fragments of B19 parvovirus VP2 capsids, which were prepared by digestion of the capsids with an endoprotease that cleaves at lysine residues.

FIG. 7B This figure shows a graphical representation of the results of colony formation assays performed on fetal liver cells that were contacted with intact B19 parvovirus VP2 capsids or fragments of B19 parvovirus VP2 capsids, which were prepared by digestion of the capsids with an endoprotease that cleaves at arginine residues.

FIG. 7C This figure shows a graphical representation of the results of colony formation assays performed on fetal liver cells that were contacted with intact B19 parvovirus VP2 capsids or fragments of B19 parvovirus VP2 capsids, which were prepared by digestion of the capsids with an endoprotease that cleaves at glutamic acid residues.

FIGS. 8A–H These figures show the results of colony formation assays conducted in the presence of pools of peptides that correspond to overlapping sequences of the B19 parvovirus VP2 capsid.

FIG. 9 This figure shows a graphical representation of the results of colony formation assays performed on fetal liver cells that were contacted with a deletion series of peptides that correspond to a P-antigen binding region of the B19 parvovirus VP2 protein.

FIG. 10 This figure shows a graphical representation of the results of 11 day colony formation assays performed on fetal liver cells that were contacted with the 10 mer NKGTQQYTDQ (SEQ. ID. NO. 5). Two experiments are shown (10 mer #1 and 10 mer #2). Colony counts in triplicate are depicted with increasing concentration of peptide plotted as a fraction of colonies formed in medium control (average of 2 triplicates=132 colonies). Peptide was added at day 4 in the same amount as at day 0. Error bars=1 SD).

FIG. 11 This figure shows a bar graph that represents the results of cell proliferation assays performed on human umbilical vein endothelial cells (HUVEC) that were contacted with varying concentrations of a control antigen (KYVTGIN) (SEQ. ID. NO. 1). On the "x axis" are increasing concentrations of the control antigen (from left to right), 0 $\mu$g/ml, 0.01 $\mu$g/ml, 0.1 $\mu$g/ml, 1.0 $\mu$g/ml, and 10.0 $\mu$g/ml. On the "y axis" are shown spectrophotometric absorbance values taken at 540 nm ($A_{540}$).

FIG. 12 This figure shows a bar graph that represents the results of cell proliferation assays performed on human umbilical vein endothelial cells (HUVEC) that were contacted with varying concentrations of B19 parvovirus capsids composed of only VP1. On the "x axis" are increasing concentrations of the B19 parvovirus capsid (VP1) (from left to right), 0 $\mu$g/ml, 0.01 $\mu$g/ml, 0.1 $\mu$g/ml, 1.0 $\mu$g/ml, and 10.0 $\mu$g/ml. On the "y axis" are shown spectrophotometric absorbance values taken at 540 nm ($A_{540}$).

FIG. 13 This figure shows a bar graph that represents the results of cell proliferation assays performed on human umbilical vein endothelial cells (HUVEC) that were contacted with varying concentrations of B19 parvovirus capsid (VP1/2). On the "x axis" are increasing concentrations of B19 parvovirus capsid (VP1/2) (from left to right), 0 $\mu$g/ml, 0.01 $\mu$g/ml, 0.1 $\mu$g/ml, 1.0 $\mu$g/ml, and 10.0 $\mu$g/ml. On the "y axis" are shown spectrophotometric absorbance values taken at 540 nm ($A_{540}$).

FIG. 14 This figure shows a bar graph that represents the results of cell proliferation assays performed on human umbilical vein endothelial cells (HUVEC) that were contacted with varying concentrations of B19 parvovirus capsid (VP2). On the "x axis" are increasing concentrations of B19 parvovirus capsid (VP2) (from left to right), 0 $\mu$g/ml, 0.01 $\mu$g/ml, 0.1 $\mu$g/ml, 1.0 $\mu$g/ml, and 10.0 $\mu$g/ml. On the "y axis" are shown spectrophotometric absorbance values taken at 540 nm ($A_{540}$).

FIG. 15 This figure shows a bar graph that represents the results of cell migration assays performed on human umbilical vein endothelial cells (HUVEC) that were contacted with varying concentrations of B19 parvovirus capsids (VP1/2), B19 parvovirus capsids having only VP1 (VP1 only), B19 parvovirus capsids having only VP2 (VP2 only), or a control antigen (control antigen).

DETAILED DESCRIPTION OF THE INVENTION

It has been discovered that the B19 parvovirus capsid, B19 parvovirus capsid proteins, or fragments thereof inhibit the growth and/or migration of cells that have a receptor that interacts with a parvovirus B19 capsid or fragment thereof (e.g., a P antigen containing cell). By using colony formation assays, it was determined that B19 parvovirus capsids composed of VP1 and VP2 or VP2 alone inhibit hematopoiesis and, thus, the growth of several different types of cells of hematopoietic origin including human fetal liver cells, human umbilical cord blood cells, and adult bone marrow cells. Using the same type of colony formation assay, it was discovered that B19 parvovirus capsids inhibit the growth of bone marrow cells obtained from Baboons and Macaques. Further, using colony formation assays, it was discovered that fragments of VP2, whether prepared by enzymatic digestion of intact VP2 capsids or by synthesis of peptides corresponding to various regions of VP2, inhibit hematopoiesis and, thus, the growth of hematopoietic cells. The tripeptide (QQY) and a 10-mer peptide (NKGTQQYTDQ SEQ. ID. NO. 5) were found to be particularly useful for the inhibition of hematopoietic cell growth, for example.

The colony formation assays used in the experiments described herein are discussed in Ek et al., *Bone Marrow*

*Transplantation* 11:395–8 (1993); Ek et aL, *Bone Marrow Transplantation* 14:9–14 (1994); Ek et al., *Fetal Diagn Therapy* 11:318–25 (1996); Ek et al., *Fetal Diagn Therapy* 11:326–34 (1996); Lindton et al., *Fetal Diagn Therapy* 15:71–78 (2000); Armitage, *Blood* 92(12):4491–4508 (1998), and Liu et al., *Blood* 90(7) 2583–2590 (1997), all of which are hereby expressly incorporated by reference in their entireties. As evidenced by the disclosure in the aforementioned references, the in vitro colony formation assays employed herein correlate with and are predictive of in vivo results. In fact, human clinical trials have been predicated on the results from colony formation assays.

Through the use of neutralization assays using monoclonal antibodies directed to the P antigen, monoclonal antibodies specific for the B19 capsid protein, and B19 parvovirus IgG positive sera obtained from two asymptomatic individuals, it was found that B19 parvovirus capsids inhibit hematopoietic cell growth by interacting with a receptor that interacts with a parvovirus B19 capsid or fragment thereof (e.g., the P antigen). Additionally, using immunolabeling, it was discovered that the B19 parvovirus capsids were internalized in cells that have a receptor that interacts with a parvovirus B19 capsid or fragment thereof (e.g., a P antigen containing cell).

It was also discovered that B19 parvovirus capsids inhibit the proliferation and migration of endothelial cells. Endothelial cell proliferation assays were performed by contacting human umbilical vein endothelial cells (HUVEC) with fibroblast growth factor in the presence of B19 parvovirus capsids. Cell proliferation was monitored by crystal violet staining and the results established that B19 parvovirus capsids effectively reduced endothelial cell proliferation. By using a Boyden chamber assay, it was determined that B19 parvovirus capsids inhibited the migration of HUVEC cells.

Several embodiments of the invention involve the manufacture of modified B19 parvovirus capsids. Many approaches to manufacture B19 parvovirus capsids having less than 5% VP1 and B19 parvovirus capsids having only VP2 are disclosed, for example. Further, the manufacture of fragments of the B19 parvovirus capsid proteins, and peptidomimetics resembling these peptides is also disclosed. These fragments can be made synthetically, by genetic engineering, and by enzymatic digestion of intact B19 parvovirus capsids. The B19 parvovirus capsids and fragments thereof can be used to inhibit the growth and or migration of cells that have the P antigen.

The peptide fragments of the invention can be at least 3 amino acids in length up to and including 780 amino acids in length and can comprise conservative amino acid substitutions. Additionally, the B19 parvovirus capsids, B19 parvovirus capsid proteins, or fragments of B19 parvovirus capsid proteins can be modified by the inclusion of substituents that are not naturally found on the B19 parvovirus capsid proteins, the inclusion of mutations, or through the creation of fusion proteins. Derivatized or synthetic B19 parvovirus capsid proteins are also embodiments.

Further, approaches to design and manufacture B19 parvovirus capsids, B19 parvovirus capsid proteins, or fragments of B19 parvovirus capsid proteins that induce a minimal immune response in a subject so as to allow for the long-term treatment protocols are described. Still further, the construction of profiles on the various B19 capsid-based therapeutics, which includes information such as sequences, sites of mutations or modifications, performance information in functional assays, and therapeutic information including disease indications, clinical evaluations and the like are embodiments of the invention.

Other embodiments of the invention include multimeric agents containing B19 parvovirus capsids, B19 parvovirus capsid proteins, or fragments of B19 parvovirus capsid proteins, including, but not limited to, the tripeptide (QQY) and a 10-mer peptide (NKGTQQYTDQ SEQ. ID. NO. 5) and methods of making these compositions. These multimeric agents (collectively referred to as "capsid agents") are created by joining B19 parvovirus capsids, B19 parvovirus capsid proteins, or fragments of B19 parvovirus capsid proteins to a support, which can be a bead, a resin, a plastic dish, and, preferably, a medical device, such as a stent, valve, or other prosthetic. In some embodiments, the capsid agents provide a potent inhibitor of the proliferation and/or migration of cells that have the P antigen (e.g., restenosis following implantation). These multimeric capsid agents can be used to inhibit cell growth and migration and also can be used to isolate cells having the P antigen (e.g., affinity chromatography).

The preparation of many different pharmaceuticals and medical devices that comprise B19 parvovirus capsids, B19 parvovirus capsid proteins, or fragments of B19 parvovirus capsid proteins is also described herein. These devices are made by joining B19 parvovirus capsids, B19 parvovirus capsid proteins, or fragments of B19 parvovirus capsid proteins or capsid agents directly or indirectly (e.g., through a linker or support) to said devices. These pharmaceuticals and medicaments can be formulated with other additives, carriers, or excipients so as to allow administration by many routes.

Therapeutic and prophylactic methods are also described. Some methods, for example, involve approaches to inhibit hematopoiesis or the proliferation and/or migration of cells that have the P antigen, including, but not limited to cells of hematopoietic origin and endothelial cells. These methods are practiced by administering a therapeutic comprising B19 parvovirus capsids, B19 parvovirus capsid proteins, or fragments of B19 parvovirus capsid proteins, preferably the tripeptide (QQY) and a 10-mer peptide (NKGTQQYTDQ SEQ. ID. NO. 5).

For example, a method to prevent or treat Polycytemia Vera is provided, wherein a subject at risk for Polycytemia Vera or a subject afflicted with Polycytemia Vera is identified and the subject is provided a therapeutically effective amount of B19 parvovirus capsid, B19 parvovirus capsid proteins, preferably VP2 capsid proteins, and fragments thereof, preferably the tripeptide (QQY) or a 10-mer peptide (NKGTQQYTDQ SEQ. ID. NO. 5). In similar methods, other hematopoietic proliferative disorders can be treated or prevented. That is, a subject in need of a capsid agent that inhibits a hematopoietic proliferative disorder is identified and said subject is provided an effective amount of B19 parvovirus capsid, B19 parvovirus capsid proteins, preferably VP2 capsid proteins, or fragments thereof, preferably the tripeptide (QQY) and a 10-mer peptide (NKGTQQYTDQ SEQ. ID. NO. 5). In some embodiments, the progress or effectiveness of treatment is monitored or measured (e.g., analysis of red blood cell hematocrit).

Embodiments of the invention also concern methods to inhibit hematopoiesis in a subject prior to in utero stem cell transplantation. These methods are practiced by providing to a subject in need of stem cell transplantation a B19 parvovirus capsids, B19 parvovirus capsid proteins, or fragments of B19 parvovirus capsid proteins, preferably the tripeptide (QQY) and a 10-mer peptide (NKGTQQYTDQ SEQ. ID. NO. 5). In a related method, hematopoiesis is inhibited in a subject prior to post natal stem cell transplantation (e.g., a novel approach to non-myeloblative therapy) by providing said subject B19 parvovirus capsids, B19 parvovirus capsid proteins, or fragments of B19 parvovirus capsid proteins, preferably the tripeptide (QQY) and a 10-mer peptide (NKGTQQYTDQ SEQ. ID. NO. 5).

Still more embodiments involve methods of preventing angiogenesis, tumorigenesis, or cancer and methods of preparing medical devices, such as stents or valves, that prevent fibrotic build up or restenosis or otherwise delay endothelial cell ingrowth. These methods are also practiced by providing B19 parvovirus capsids, B19 parvovirus capsid proteins, or fragments of B19 parvovirus capsid proteins, preferably the tripeptide (QQY) and a 10-mer peptide (NKGTQQYTDQ SEQ. ID. NO. 5) to a subject at risk of angiogenesis, tumorigenesis, or cancer or to a medical device such as a stent or valve.

Kits comprising B19 parvovirus capsids, B19 parvovirus capsid proteins, or fragments of B19 parvovirus capsid proteins preferably the tripeptide (QQY) and a 10-mer peptide (NKGTQQYTDQ SEQ. ID. NO. 5) are also embodiments of the invention. These kits may contain instructions relating to dosage and time of administration. These kits may also have a device to remove blood from a subject and/or a device to measure blood hematocrit or endothelial cell growth. The section below describes the experiments that provided evidence that B19 parvovirus capsids inhibit the growth of hematopoietic cells.

B19 Parvovirus Capsids Inhibit Hematopoiesis and the Growth of Hematopoietic Cells In a first set of experiments, it was discovered that B19 parvovirus capsids inhibit hematopoiesis and that these molecules could be used to reduce the overproduction of red blood cells, white blood cells, and blood platelets, as is experienced by patients suffering from hematological proliferative diseases, such as Polycytemia Vera. (See FIG. 1A). In a first set of experiments, fresh human fetal liver cells, umbilical cord blood cells, and bone marrow cells were contacted with recombinant B19 parvovirus capsids in a colony formation assay. The general features of a colony formation assay are depicted in FIG. 1B. The ability of the B19 parvovirus capsids to inhibit hematopoiesis was verified by the reduction of colony formation in the presence of the capsids, as compared to untreated control populations of cells. A more detailed description of these experiments is provided below.

To obtain fetal liver tissue, human fetuses 6–12 weeks of gestational age were obtained from legal abortions; the patients had volunteered to donate fetal tissue. Gestational age was estimated according to specific anatomical markers and is given as menstruational age. Abortions were performed with vacuum aspirations. Fetal liver was dissected under sterile conditions, placed in a sterile tube containing RPMI1640 and disintegrated by passage through a vinyl mesh to form a single cell suspension. Nucleated cells were then washed three times, counted and diluted in culture medium.

A commercial kit—the "Stem cell CFU kit" (GIBCO BRL, Life Technology Inc., NY, USA)—was used to perform the colony formation assays. The kit provides a semisolid support that mimics the extracellular matrix produced by stromal cells. Other components included in the kit are: Iscove's modified Dulbecco's medium, modified fetal bovine serum, methylcellulose, 2-mercaptoethanol, conditioned medium and erythropoietin. The colonies that were formed in the assay were identified as BFU-E (burst forming unit-erythroid cells) with densely packed hemoglobonized cells, CFU-GM (colony forming units-granulocytes, macrophages) with arrangements of non-hemoglobinized cells, and CFU-GEMM (colony forming units-granulocytes, erythroid cells, macrophages, megakaryocytes) with hemoglobinized cells and small and large peripheral cells.

Recombinant B19 parvovirus empty capsid particles (Kajigaya et al., *Proc Natl Acad Sci USA,* 88:4646 (1991)) were prepared in a recombinant baculovirus-insect cell (*Spodofera frugiperda*) expression system. (Kajigaya et al., *Proc Natl Acad Sci USA,* 88:4646 (1991)). The isolated or purified capsids were diluted in buffer (20 mM Tris, 0.5M NaCl, pH 8.5) and 30 $\mu$L of each dilution was added to approximately $25\times10^3$ cells ($50\times10^3$ for postnatal cells) in 100 $\mu$L of culture medium and incubated for 1 hour at 4° C. The mixtures were then transferred to incubation dishes and culture medium was added to a final volume of 0.5 ml per well. The cells were then incubated for 11 days in a humidified atmosphere at 5% $CO_2$, and were scored for BFU-E, CFU-GM and CFU-GEMM derived colony formation.

In the 11-day colony formation assay, described above, it was found that B19 parvovirus capsids inhibited hematopoietic cell growth, as evidenced by a reduction in colony formation of fresh human fetal liver cells, umbilical cord blood cells, and adult bone marrow cells. That is, a reduction in colony formation of BFU-E (burst forming unit-erythroid), CFU-GM (colony forming unit-granulocyte, macrophage) and CFU-GEMM (colony forming unit-granulocyte, erythrocyte, monocyte, megakaryocyte) cells was observed when human fetal liver cells, umbilical cord blood cells, and adult bone marrow cells were incubated with the B19 parvovirus capsids. (See Table 1).

TABLE 1

Colony-forming unit assay of fetal liver cells*.

| Dilution of B19 parvovirus capsid ($\mu$g/ml) | Colony Counts (% of medium control) BFU-E | CFU-GM | CFU-GEMM |
|---|---|---|---|
| 70.0 | 22% | 14% | 31% |
| 0.7 | 39% | 54% | 63% |
| 0.007 | 79% | 95% | 94% |
| Medium (= 100%), counts | 95 | 37 | 16 |

*The cells were pre-incubated with dilutions of the B19 parvovirus capsids prior to the 11 day culture.

As shown in Table 1, an inhibition of the colony formation of hematopoietic cells was seen with as little as 0.007 $\mu$g/ml B19 parvovirus capsid and considerable inhibition was observed at 70.0 $\mu$g/ml B19 parvovirus capsid. Recombinant papillomavirus capsids (Cottontail rabbit papillomavirus and human papillomavirus type 6) were included in the colony formation assays as controls. These control capsids are structurally similar to parvovirus capsids but do not interact with the P antigen. The control capsids (tested in the range 0.01–100 $\mu$g/ml) had no effect on colony formation.

In other experiments, it was found that the colony formation of hematopoietic cells could be rescued by incubating B19 parvovirus capsids with anti-B19 parvovirus monoclonal antibodies or with B19 parvovirus IgG positive human sera, prior to adding the mixture to the cells. The anti-B19 parvovirus monoclonal antibody (MAB8292), which is an IgG class antibody, was purchased (Chemicon AB, Malmo, Sweden) and the B19 parvovirus IgG positive (B19 parvovirus IgM negative) sera were obtained from two asymptomatic individuals. In one neutralization experiment, B19 parvovirus capsids were incubated with anti-B19 parvovirus monoclonal antibody (MAB8292) prior to adding the mixture to fetal liver cells. Approximately, 25 μl of anti-B19 parvovirus monoclonal antibody (MAB8292) was incubated with 25 μl of B19 parvovirus capsids for 2 hours at 4° C. The mixtures were then added to the cells and the 11-day colony formation assay, as described above, was performed on the "neutralized"-capsid/cell mixture.

Although a relatively high concentration of B19 parvovirus capsids was used (7 μg/ml, as compared to the values in Table 1), as little as 0.02 μg/ml of the anti-B19 monoclonal antibody reduced the ability of B19 parvovirus capsids to inhibit colony formation and a concentration of 20.0 μg/ml of the anti-B19 parvovirus monoclonal antibody completely blocked the inhibition on BFU-E colony formation and drastically reduced the effect on CFU-GM and CFU-GEMM colony formation (See Table 2).

TABLE 2

Neutralization assay using anti-B19 parvovirus monoclonal antibody*.

| B19 parvovirus capsid (7 μg/ml) + dilutions of Anti-B19 parvovirus | Colony Counts (% of medium control) | | |
|---|---|---|---|
| Mab (μg/mL) | BFU-E | CFU-GM | CFU-GEMM |
| 20.0 | >100% | 74% | 67% |
| 2.0 | 69% | 35% | 45% |
| 0.2 | 52% | 21% | 19% |
| 0.02 | 52% | 30% | 21% |
| capsid only | 43% | 30% | 21% |
| Medium (= 100%), counts | 114 | 66 | 42 |

*The cells were pre-incubated with the reagents prior to the 11 day culture.

Similarly, the two lots of B19 parvovirus IgG positive sera were analyzed for their ability to neutralize the B19 parvovirus capsids. Approximately, 25 μl of B19 parvovirus IgG positive serum was incubated with 25 μl of B19 parvovirus capsids for 2 hours at 4° C., then the mixtures were added to fetal liver cells. Subsequently, the colony formation assay described above was performed on the sera-neutralized B19 parvovirus capsid/cell mixture. As shown in Table 3, in the absence of sera, B19 parvovirus capsids (0.14 μg/ml) significantly inhibited fetal liver cell colony formation, whereas, as little as a 1:100 dilution of serum 1 reduced the ability of B19 parvovirus capsids to inhibit fetal liver cell growth.

TABLE 3

Neutralization assay using human B19 parvovirus IgG positive sera*.

| B19 parvovirus capsid (0.14 μg/ml) + dilutions of two human | Colony Counts (% of medium control) | | |
|---|---|---|---|
| B19 parvovirus IgG positive sera | BFU-E | CFU-GM | CFU-GEMM |
| Serum 1, 1:10 | 70% | 78% | 90% |
| Serum 1, 1:100 | 25% | 23% | 40% |
| Serum 2, 1:10 | 48% | 57% | 57% |
| Serum 2, 1:100 | 17% | 27% | 67% |
| capsid only | 18% | 17% | 63% |
| Medium (= 100%), counts | 157 | 81 | 30 |

*The cells were pre-incubated with the reagents prior to the 11 day culture.

Further evidence that B19 parvovirus capsids inhibit the colony formation of hematopoietic cells was obtained by performing neutralization assays using monoclonal antibodies directed to the P-antigen. The anti-P monoclonal antibody (CLB-ery-2), is a mouse IgM class antibody. (See von dem Borne et al., *Br J Hematol,* 63:35 (1986), herein expressly incorporated by reference in its entirety). In these assays, approximately $2.5\times10^4$ fetal liver cells were suspended in 100 μl of medium and were then incubated with either 25 μl of anti-P monoclonal antibody (CLB-ery-2) or 25 μl of anti-PI (Seraclone), a control monoclonal antibody. Cells and monoclonal antibody were incubated for 1 hour at 4° C. The cell/antibody mixtures were washed twice in cold culture medium prior to adding the B19 parvovirus capsids and, subsequently, the colony formation assays were conducted, as previously described.

In accord with the evidence from the previous experiments and studies conducted with native viral particles (See Brown et al., *Science,* 262:114 (1993)), it was discovered that the monoclonal antibodies directed to the P antigen could restore growth of fresh fetal liver cells incubated in the presence of B19 parvovirus capsids. As shown in Table 4, the inhibitory effect of the B19 parvovirus capsid was reduced by at least 25% when the cells were incubated in the presence of CLB-ery-2. In contrast, the anti-$P_1$ (Seraclone) monoclonal antibody (Labdesign, Stockholm, Sweden), which does not interact with the P antigen, had no effect on colony formation as compared to the B19 parvovirus capsid control.

TABLE 4

Neutralization assay using anti-P or anti$P_1$ monoclonal antibodies*.

| | Colony Counts (% of medium control) | | |
|---|---|---|---|
| | BFU-E | CFU-GM | CFU-GEMM |
| B19 parvovirus capsid (0.14 μg/ml) + of Anti-P Mab (titer) | | | |
| 1:5 | 51% | 39% | 93% |
| 1:500 | 23% | 10% | 43% |
| capsid only | 18% | 17% | 63% |
| Medium (= 100%), counts | 157 | 81 | 30 |
| B19 parvovirus capsid (0.14 μg/mL) + of Anti-$P_1$ Mab (μg/ml) | | | |
| 400.0 | 25% | 20% | 50% |
| 4.0 | 17% | 22% | 47% |
| capsid only | 18% | 17% | 63% |
| Medium (= 100%), counts | 157 | 81 | 30 |

*The cells were pre-incubated with the reagents prior to the 11 day culture.

The inhibitory effect of B19 parvovirus capsids on colony formation was also tested using fresh stem cells derived from cord blood and adult bone marrow samples. Colony formation assays in the presence of B19 parvovirus capsids were performed on cells obtained from umbilical cord blood and bone marrow using the protocol described above. Umbilical cord blood samples were obtained immediately after vaginal delivery from normal births. Samples of adult bone marrow were obtained from healthy allogeneic donors. Suspensions of fresh cells were heparinized and diluted in 0.9% NaCl and separated on Lymphoprep (Nycomed, Parma, Oslo, Norway) for gradient centrifugation at 2000 rpm for 20 min. Cells were carefully removed with a Pasteur pipette, washed three times in 0.9% NaCl, counted and diluted in culture medium in preparation for the colony formation assays.

The ability of B19 parvovirus capsids to inhibit hematopoietic cells obtained from cord blood and bone marrow was comparable to that exhibited with fetal liver cells (See Table 5). As shown in FIG. 1C, for example, the growth of cells obtained from human cord blood decreased as the concentration of B19 parvovirus capsid increased. Further, neutralization assays using cells obtained from cord blood or bone marrow and B19 parvovirus capsids also exhibited results similar to those seen with human fetal liver cells. That is, B19 parvovirus capsids that were incubated with the anti-B19 parvovirus monoclonal antibody (Mab8292) prior to contact with the cells obtained from cord blood and bone marrow demonstrated a reduced ability to inhibit cell growth, as evidenced by an increase in colony formation.

TABLE 5

Colony formation assay on cord blood and adult bone marrow cells

| B19 parvovirus capsid (µg/ml) | Colony Counts (% of medium control) | | |
|---|---|---|---|
| | BFU-E | CFU-GM | CFU-GEMM |
| Cord blood cells | | | |
| 7.0 | 10% | 54% | 43% |
| 0.7 | 33% | 62% | 43% |
| 0.07 | 49% | 72% | 50% |
| 0.007 | 57% | 67% | 70% |
| 0.0007 | 84% | 79% | 93% |
| Medium (= 100%), counts | 134 | 39 | 30 |
| Bone marrow cells | | | |
| 7.0 | 18% | 36% | 6% |
| 0.7 | 43% | 45% | 28% |
| 0.07 | 63% | 41% | 44% |
| 0.007 | 76% | 80% | 78% |
| 0.0007 | 86% | 77% | 78% |
| Medium (= 100%), counts | 134 | 39 | 30 |

*The cells were incubated with dilutions of B19 parvovirus capsid (µg/mL) prior to the 11 day culture.

Additionally, colony formation assays in the presence of B19 parvovirus cells were performed, as described above, using hematopoietic cells obtained from the bone marrow of monkeys (Baboons and Macaques). As shown in FIG. 2, primate hematopoietic cell growth decreased in concordance with an increase in concentration of B19 parvovirus capsid. The results from this experiment not only demonstrate that primate hematopoietic cells have a receptor that interacts with B19 parvovirus capsids but also established that Baboon and Macaque primates are suitable for in vivo study of the therapeutic and prophylactic embodiments of the invention.

In an effort to identify the regions of the B19 parvovirus capsid that are involved in inhibiting cell growth, it was observed that after binding, the capsid fuses with cells having the P antigen and then becomes internalized. In one experiment that provided evidence of B19 parvovirus capsid internalization, fetal liver cells were incubated with B19 parvovirus capsids and the capsid treated cells were fixed on BioRad slides, labeled with the anti-B19 parvovirus monoclonal antibody (Mab8292), and detected with a fluorescent secondary antibody. By this approach, fetal liver cells were washed in PBS and a suspension with a cell concentration of approximately $2 \times 10^6$/ml was prepared. A fraction of the suspension was incubated with B19 parvovirus native capsid, (0.35 µg capsid/ml cell suspension), in 37° C. for 1 hour. Approximately, 20 µl droplets (about 40,000 cells) of cell/capsid suspension was then placed on two BioRad slides, 10 wells on each slide. In two of the wells on each slide, cells that had not been treated with capsids were used as controls.

Next, the cells on one of the two BioRad® slides were permeablized with saponine, which promotes antibody penetration. Subsequently, primary anti-B19 parvovirus monoclonal IgG antibody was added and, after binding and removal of unbound primary antibody with a PBS wash, the secondary fluorescent anti-IgG antibody was added, allowed to bind, and the unbound secondary antibody was removed with a PBS wash. A UV-light microscope was used for the analysis. Saponin permeablized cells treated with B19 parvovirus capsids exhibited fluorescence on cell membranes and inside the cells. In contrast, control cells, which were not permeablized with saponin, exhibited fluorescence only at the cell surface. These results provided evidence that the inhibition of cell growth mediated by the B19 parvovirus capsid may involve more than a receptor/ligand interaction. The next section describes the discovery that modified B19 parvovirus capsids can be used to inhibit hematopoiesis and/or hematopoietic cell growth.

Modified B19 parvovirus capsids inhibit hemaptopoiesis and hematopoietic cell growth Although some embodiments of the invention comprise B19 parvovirus capsids without modification, native B19 parvovirus VLPs (i.e., capsids having 95% VP2 and 5%VP1) elicit an immune response, which makes them less desirable for some therapeutic applications (e.g., use in long term treatment protocols), others have constructed a modified B19 parvovirus capsid having 25% VP1 and 75% VP2 while trying to develop a parvovirus vaccine, however, this modified VLP induces an elevated neutralizing response in vivo. (See U.S. Pat. No. 5,508,186 to Young et al., herein expressly incorporated by reference in its entirety). Such modified B19 parvovirus capsids are undesirable for long-term therapeutic protocols because a subject's immune response can quickly clear the VLPs from the subject's body, thus, lowering the effective dose. Additionally, since the seroprevalence of antibodies to parvovirus in the population approaches 50–70%, it is preferred that treatment protocols use capsid agents that elicit a minimal immune response.

Since the unique region of VP1 appears to play an integral role in immune response to the B19 parvovirus capsid (See Fields et al., *Virology vol.* 2, 3rd edition, Lipponcott-Raven Publishers, Philidelphia, Pa., p. 2207 (1996)), modified capsids that comprise less VP1 than is found in nature can be manufactured and can be more effective therapeutics for long term use. Thus, some embodiments include B19 parvovirus capsids that comprise, consist essentially of, or consist of an amount of VP1 that is less than or equal to about 0.1% to about 5.0%. That is, the amount of VP1 can be about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, and 5.0% of the total amount of VP1 and VP2.

Further, recombinant VP2 can spontaneously form capsid structures that are similar to the VP1/VP2 structure without VP1. (See U.S. Pat. No. 5,508,186 to Young et al.). The VP2 capsids have only minor neutralizing regions and, thus, can be very effective therapeutics for use in long-term treatment protocols. Thus, some embodiments include B19 parvovirus capsids that comprise, consist essentially of, or consist of an amount of VP2 that is about 95% or more; that is, more than or equal to 100%, 99.5%, 99%, 98.5%, 98%, 97.5%, 97%, 96.5%, 96%, 95.5%, and 95% of the total amount of VP1 and VP2.

By employing the colony formation assays described above, it was discovered that VP2 capsids can also inhibit hematopoiesis and the growth of hematopoietic cells. (See FIG. 3). As above, human fetal liver cells were incubated in the presence of the VP2 capsids and the 11 day colony formation assay was performed. The positive control in these experiments was the native B19 parvovirus VLP, that is, the B19 parvovirus capsids having 95% VP2 and 5% VP1 (VP1/2). The results shown in FIG. 3 verify that the VP2 capsids inhibit hematopoietic cell growth at concentrations as low as 3 μg/ml and significant inhibition occurs at 30 μg/ml.

In a similar experiment, it was determined that B19 parvovirus VP2 capsids (8.3.2000 VP2) inhibited colony formation of hematopoietic stem cells as effectively as VP1/2 capsids (See FIG. 4). Approximately 50% inhibition was seen at 1 μg/ml VP2 capsid, whereas approximately 40% inhibition (60% of the medium control) was seen at 0.07 μg/ml VP1/2 capsid. (See FIG. 3). In these experiments, fetal liver cells were incubated with dilutions of the B19 parvovirus capsids prior to the 11-day colony formation assay. Data are plotted in comparison with the medium control (the medium control being 1.0) and represent four different experiments, each one in triplicate (mean +/−1 SD).

Recombinant VP2 capsid proteins derived from a canine parvovirus (CPV) strain (denoted 5) did not inhibit colony formation in assays where VP2 capsids (8.3.2000) reduced colony formation to less than 30% of the control. (See FIG. 5). The effect of B19 parvovirus VP2 capsids ("8.3.2000", 30 μg/mL) and CPV (canine parvovirus) VP2 capsids ("5", 30 μg/mL) in a colony-forming unit assay of fetal liver cells is shown in FIG. 5. The cells were incubated with the capsids prior to the 11-day colony formation assay. Data are plotted in comparison with the medium control (the medium control being 1.0) and represent two different experiments (gray and black bars, respectively), each one in triplicate (mean+/−1 SD). The CPV capsids were baculovirus-produced (in Sf-9 cell cultures) and were purified by ultracentrifugation for one hour. The results above provided strong evidence that B19 VP2 capsids inhibit hematopoiesis and the proliferation of cells having the P antigen.

To verify that the B19 parvovirus VP2 capsids were, in fact, the agent responsible for the inhibition of cell growth, neutralization assays, as described above, were conducted. As described for the B19 parvovirus VP1/VP2 constructs, Lindton et al., *Fetal Diagn. Ther.* 16(1):26–31 (2001), herein expressly incorporated by reference in its entirety, the inhibitory effect of the VP2 protein on colony formation was partially neutralized by a monoclonal antibody directed to the VP1/VP2 protein (See FIG. 6). In these experiments, B19 parvovirus VP2 capsids were incubated with different dilutions of an anti-B19 parvovirus monoclonal antibody (MAB 8292 obtained from Chemicon) and were then incubated with fetal liver cells prior to the colony-formation assay. The data in FIG. 6 are plotted in comparison with the medium control (the medium control being 1.0) and represent four different experiments, each one in triplicate (mean+/−1 SD). Two donors of fetal liver cells were used for comparison (#1 and #2, respectively). Although a total neutralizing effect was not reached, which may be due to the fact that the monoclonal antibody is not specific to the VP2 protein alone, the data from this experiment verified the inhibition of colony formation mediated by the B19 parvovirus VP2 capsids. The section below describes the discovery that fragments of the B19 parvovirus VP2 capsid inhibit hematopoiesis and the growth of cells that have the P antigen.

Fragments of B19 Parvovirus VP2 Capsids Inhibit Hemaptopoiesis and Hematopoietic Cell Growth In addition to intact B19 parvovirus VP2 capsids, fragments of B19 parvovirus VP2 capsids can be used to inhibit hematopoiesis and the growth of P antigen containing cells. In another set of experiments, B19 parvovirus VP2 capsids were enzymatically cleaved and the resulting cleavage products were found to inhibit hematopoiesis in colony formation assays. (See FIGS. 7A–C). In these experiments, B19 parvovirus VP2 capsids were digested with three different endoproteases: LYS-C endoprotease sequencing grade; ARG-C endoprotease sequencing grade; and GLU-C endoprotease sequencing grade obtained from Roche. The cleavage products were contacted with fetal liver cells, which were then subjected to a colony formation assay. That is, the cells were incubated with various dilutions of the B19 parvovirus VP2 fragments prior to the 11-day colony formation assay, as described above. Data are plotted as a percentage of the medium control (the medium control being 1.0) and represent one experiment, performed in triplicate (mean+/−1 SD). Silver staining of a gel in which the cleavage products were separated confirmed that no intact B19 parvovirus VP2 capsid remained. The data show that the cleavage products created by digestion with an endoprotease that cleaves at either Lysine residues or Arginine residues but not at Glutamic acid residues are fragments of B19 parvovirus VP2 capsid protein that effectively inhibit colony formation. Additionally, the data showed that specific fragments or regions of the VP2 protein may be involved in producing the inhibitory effect.

Figure 8A:
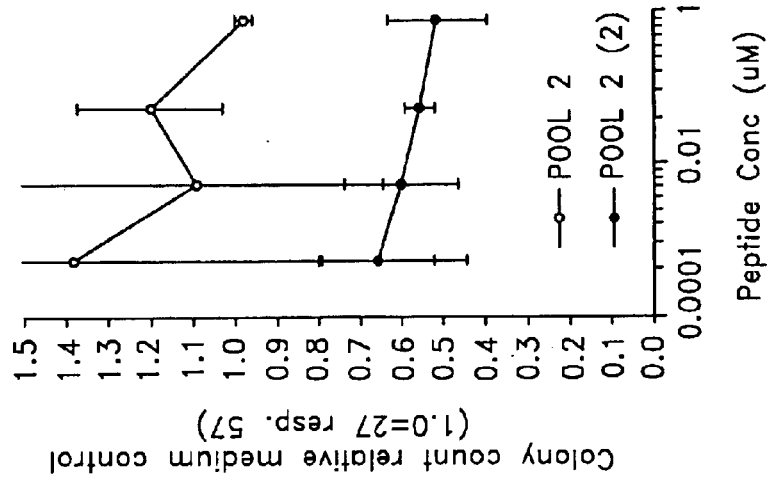
Figure 8B:
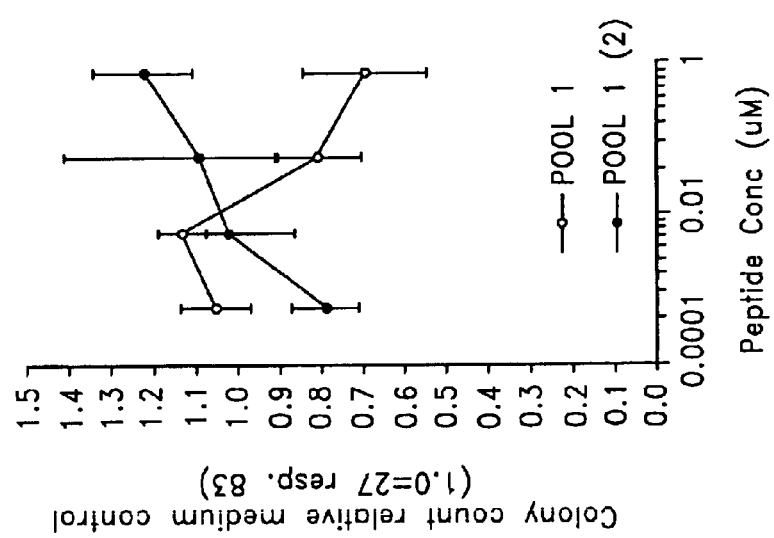
Figure 8C:
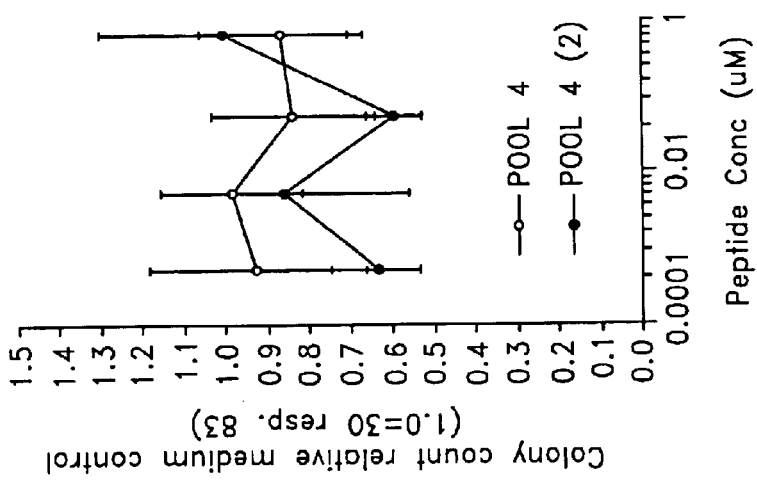
Figure 8D:
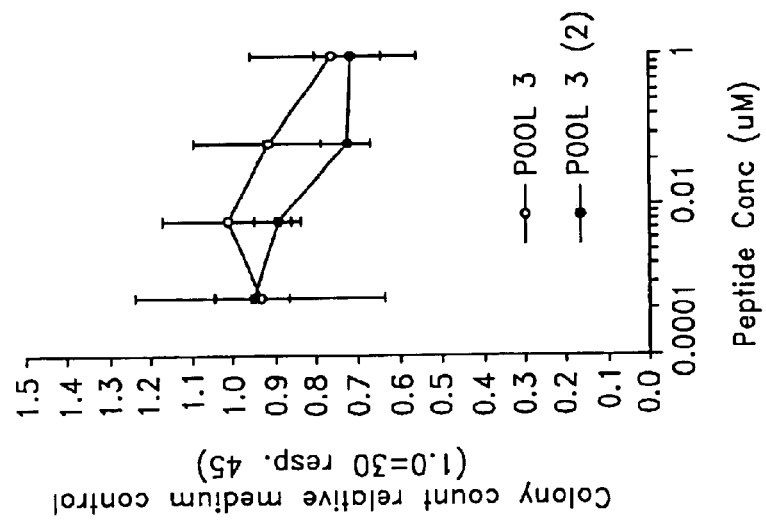
Figure 8E:
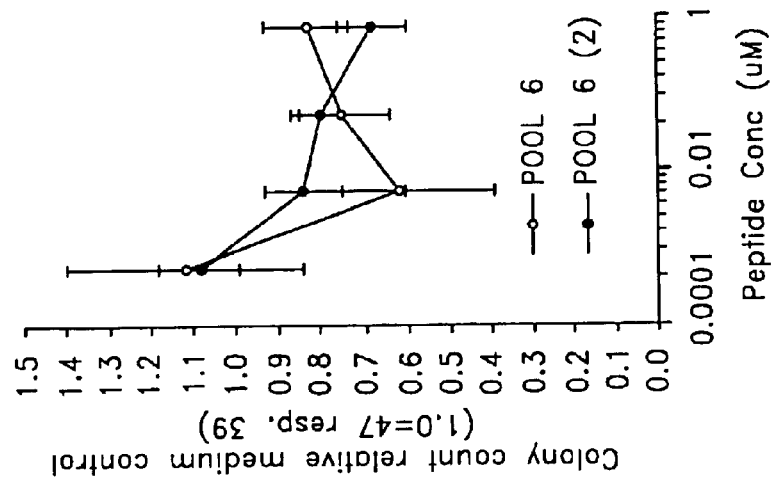
Figure 8F:
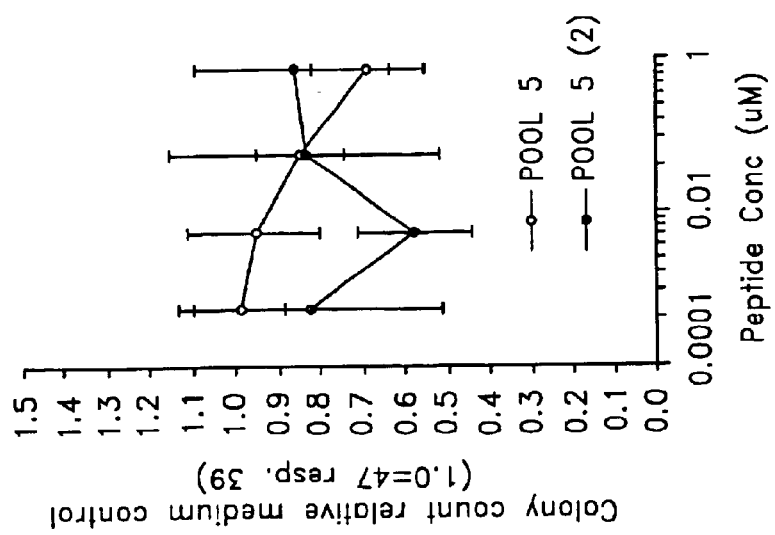
Figure 8G:
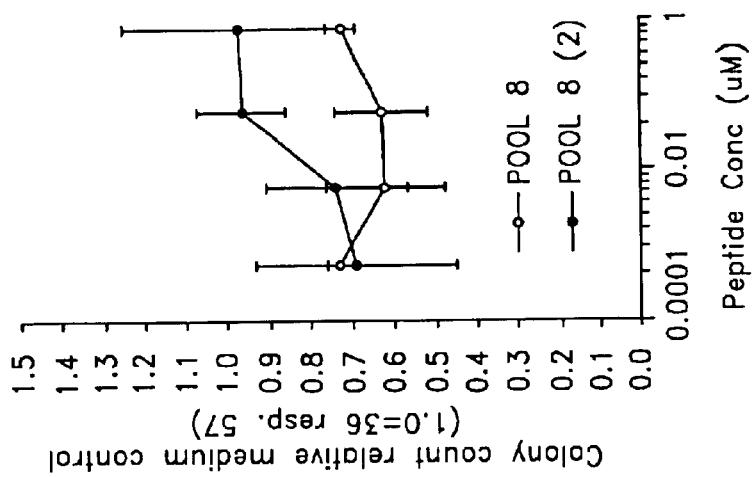
Figure 8H:
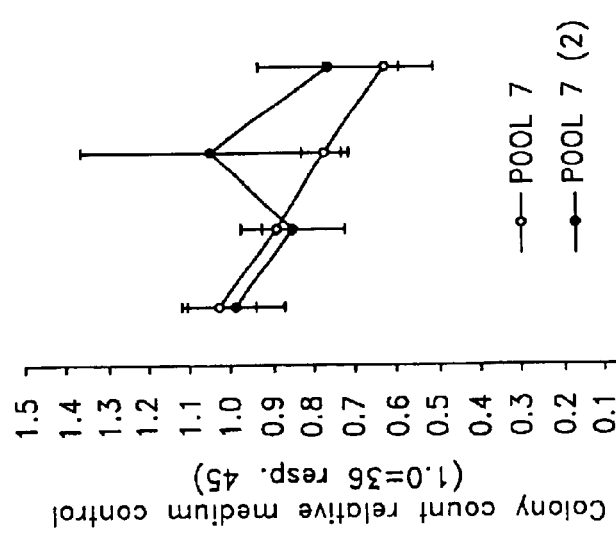
Figure 9:
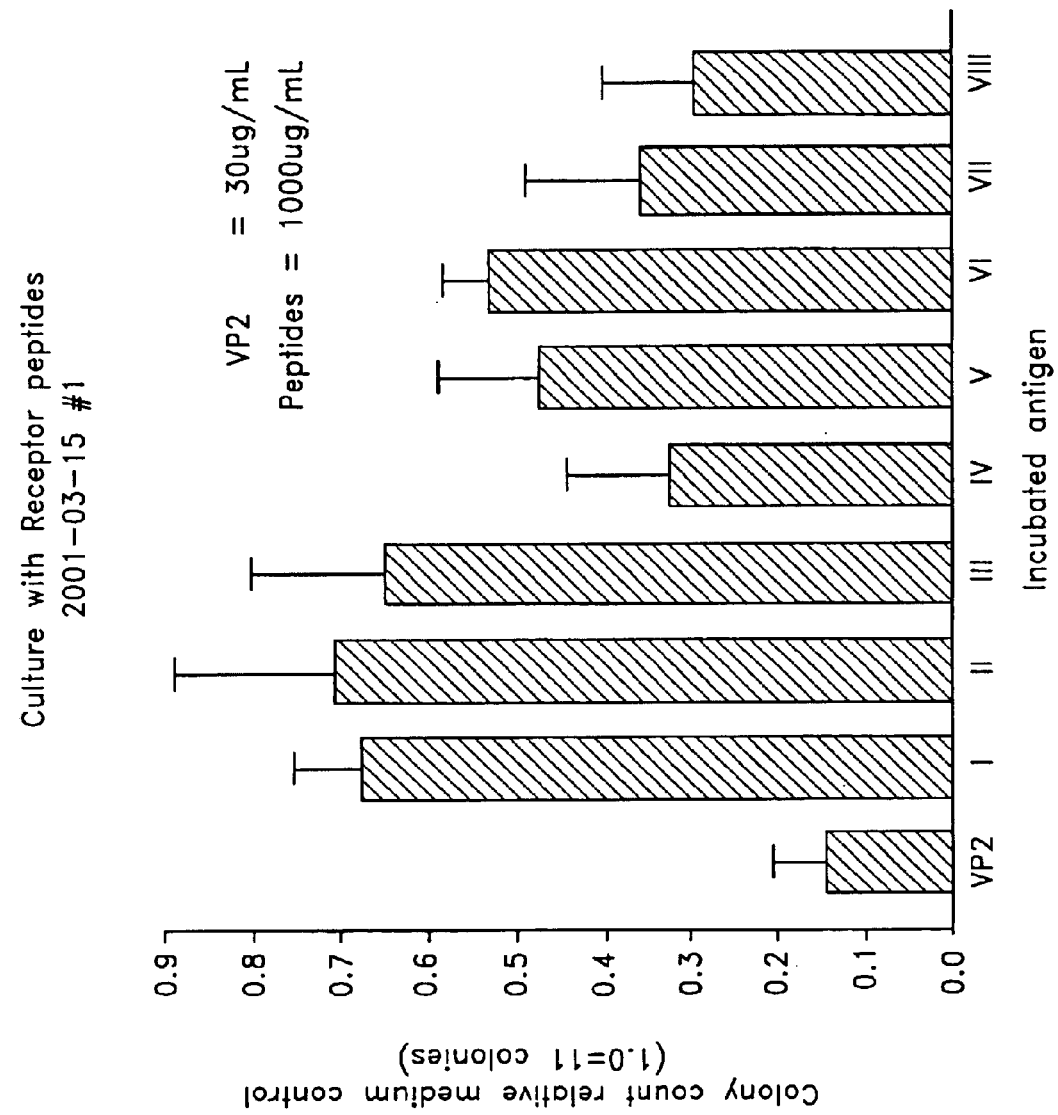
Figure 10:
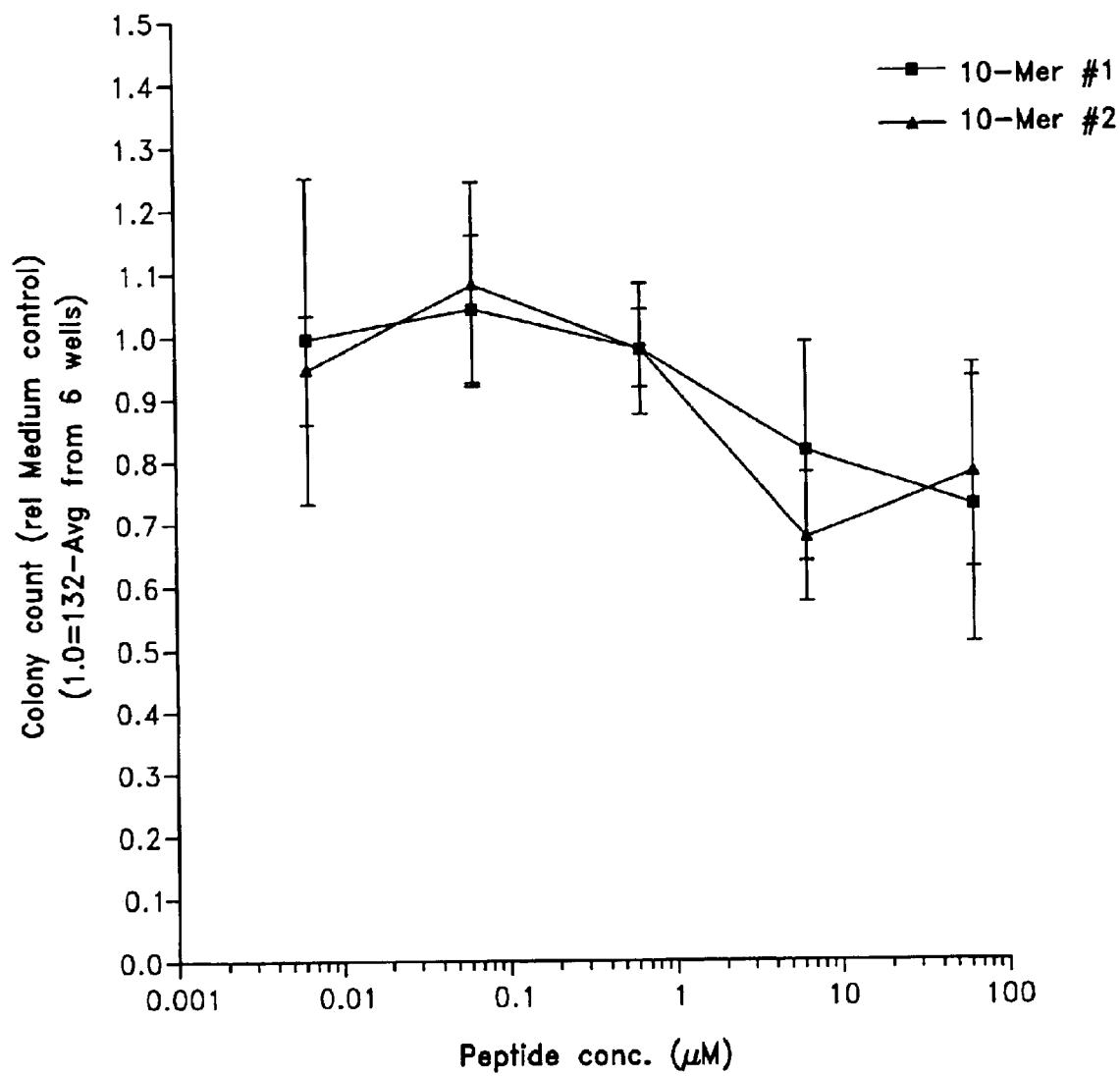
Figure 11:
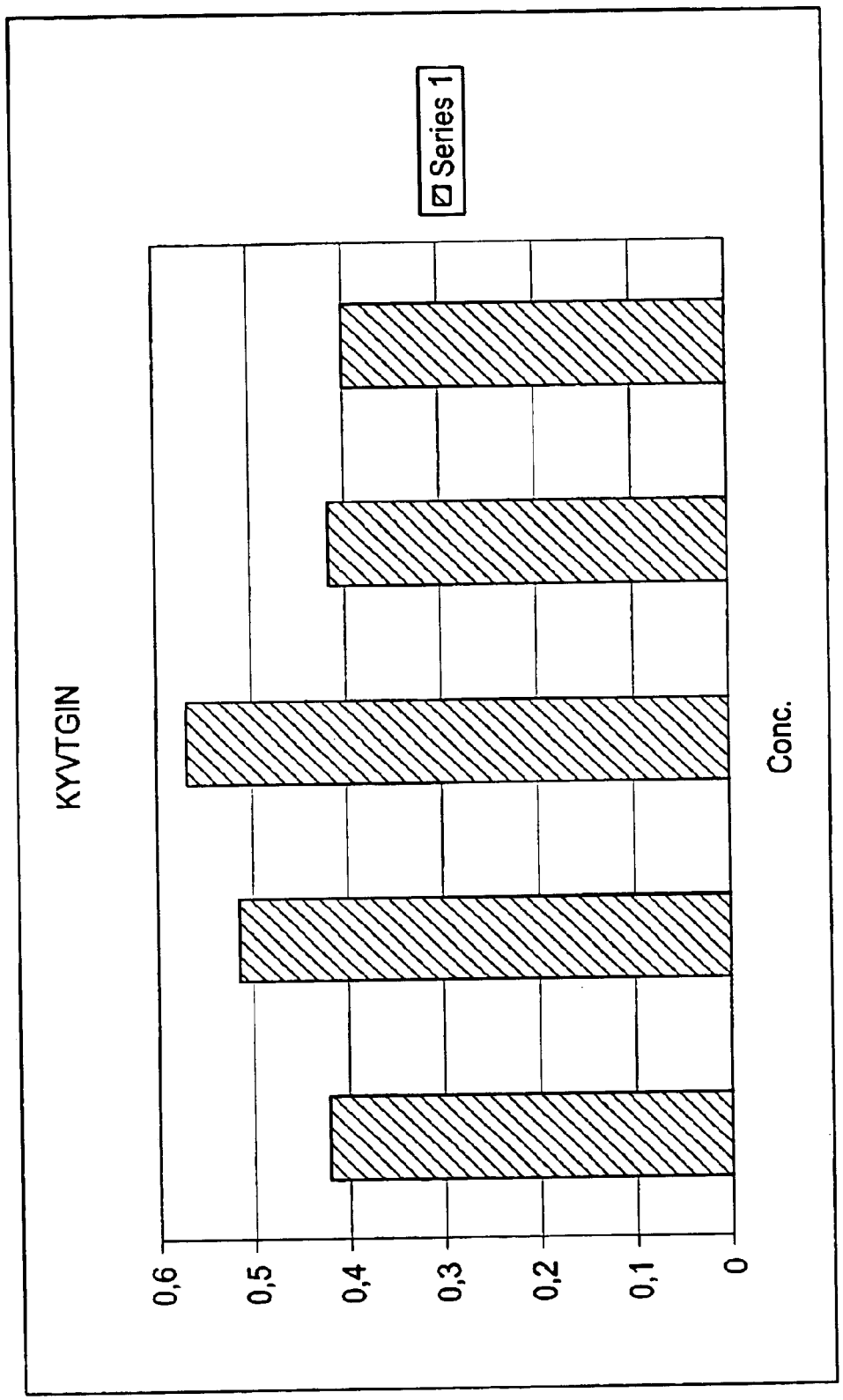
Figure 12:
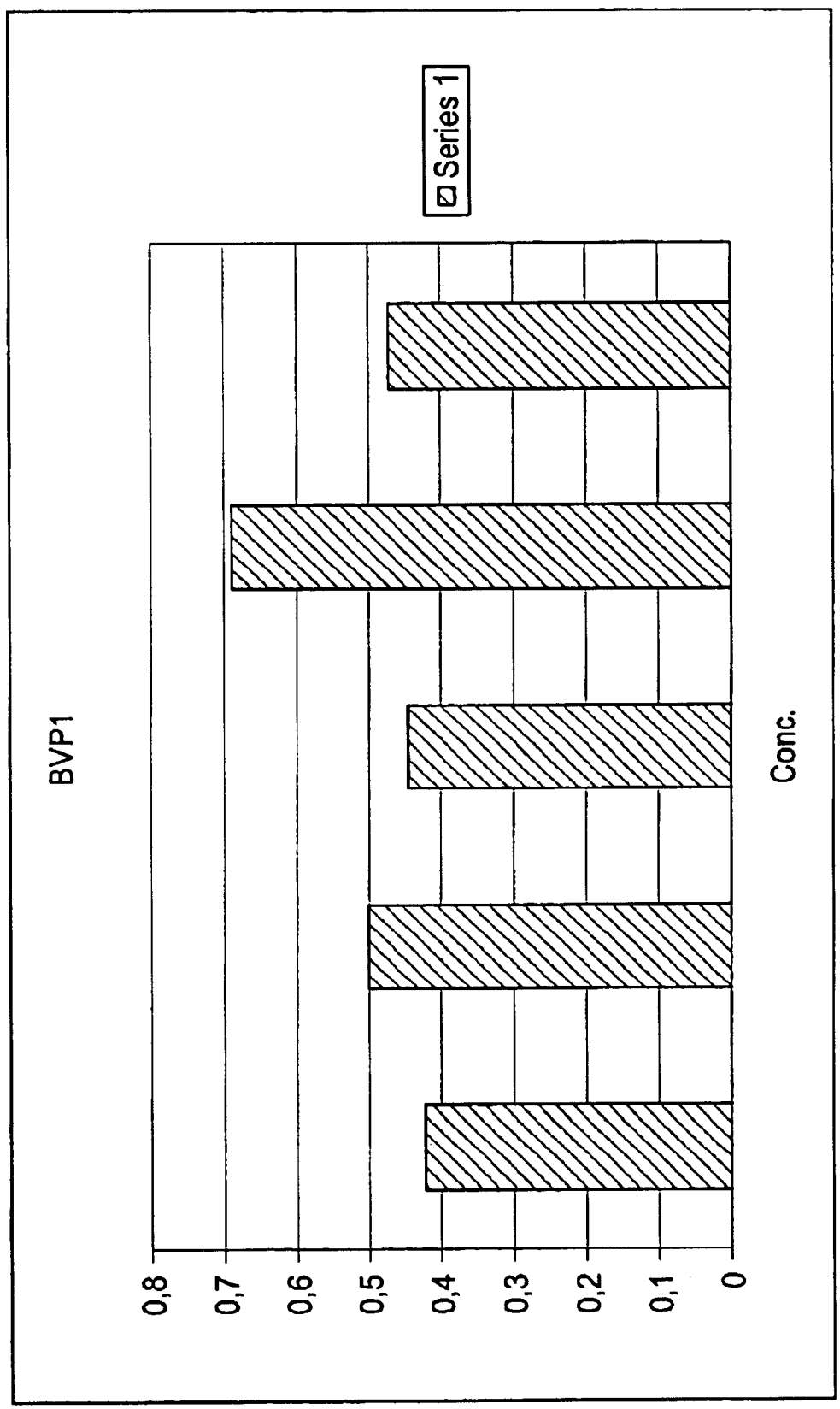
Figure 13:
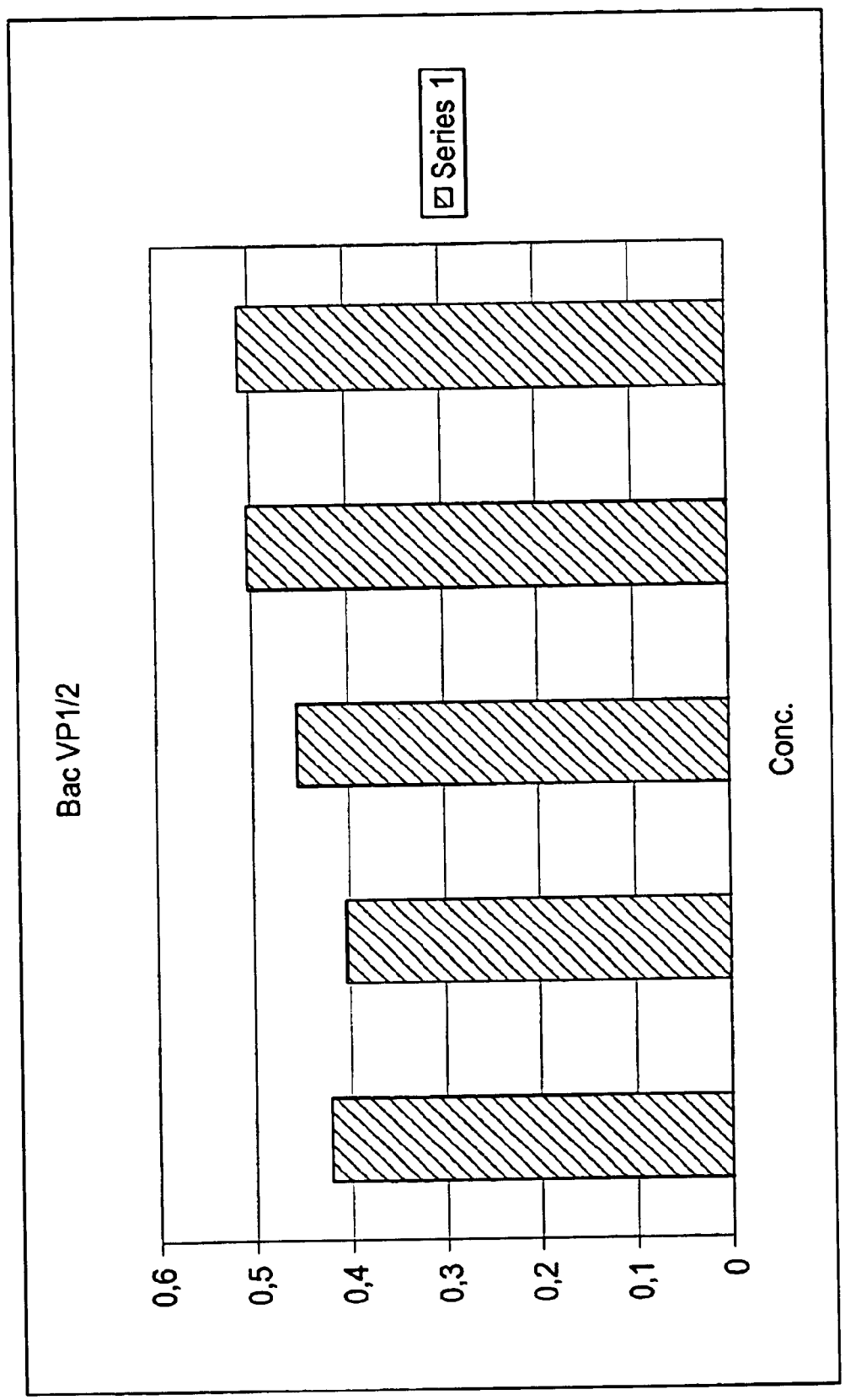
Figure 14:
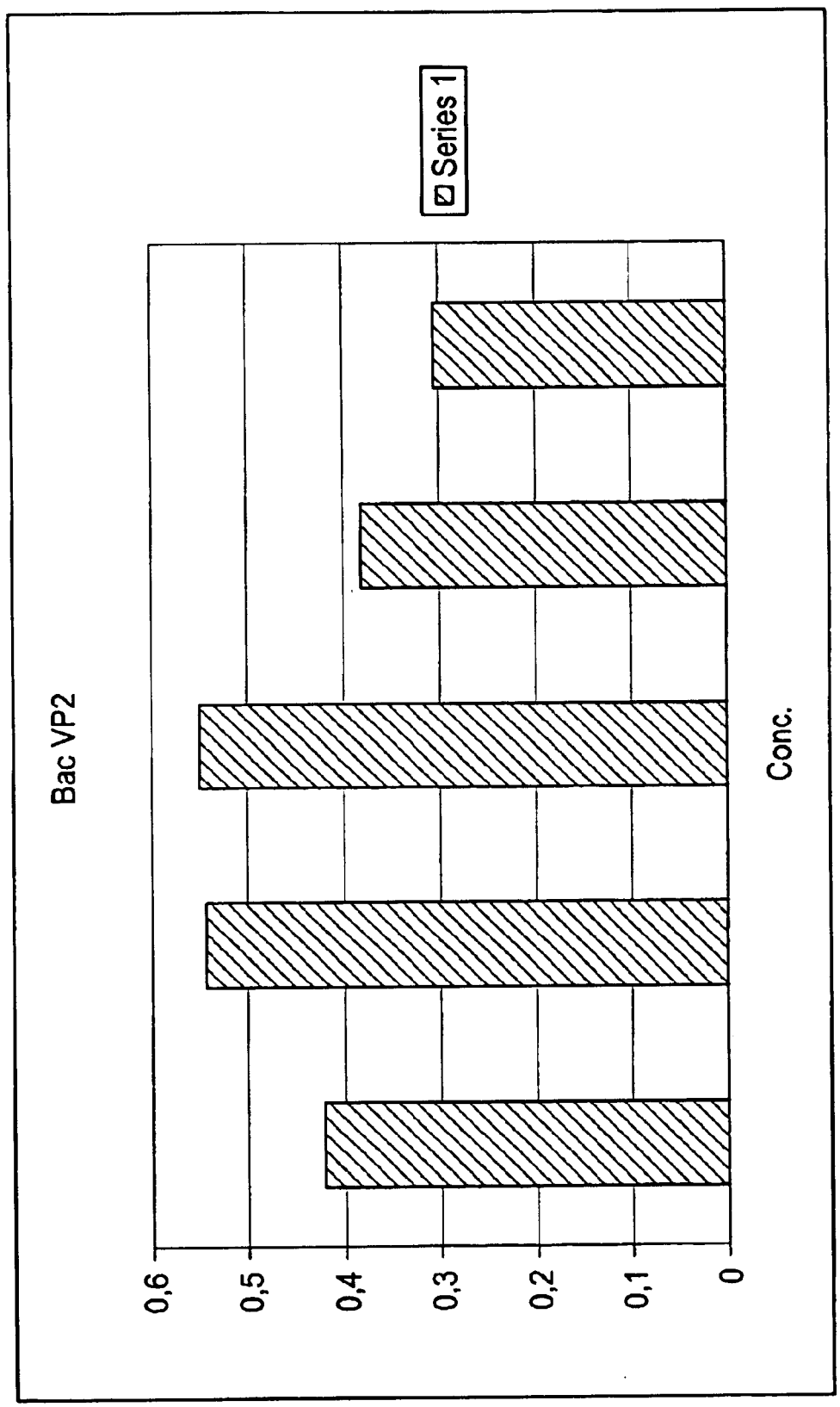
Figure 15:
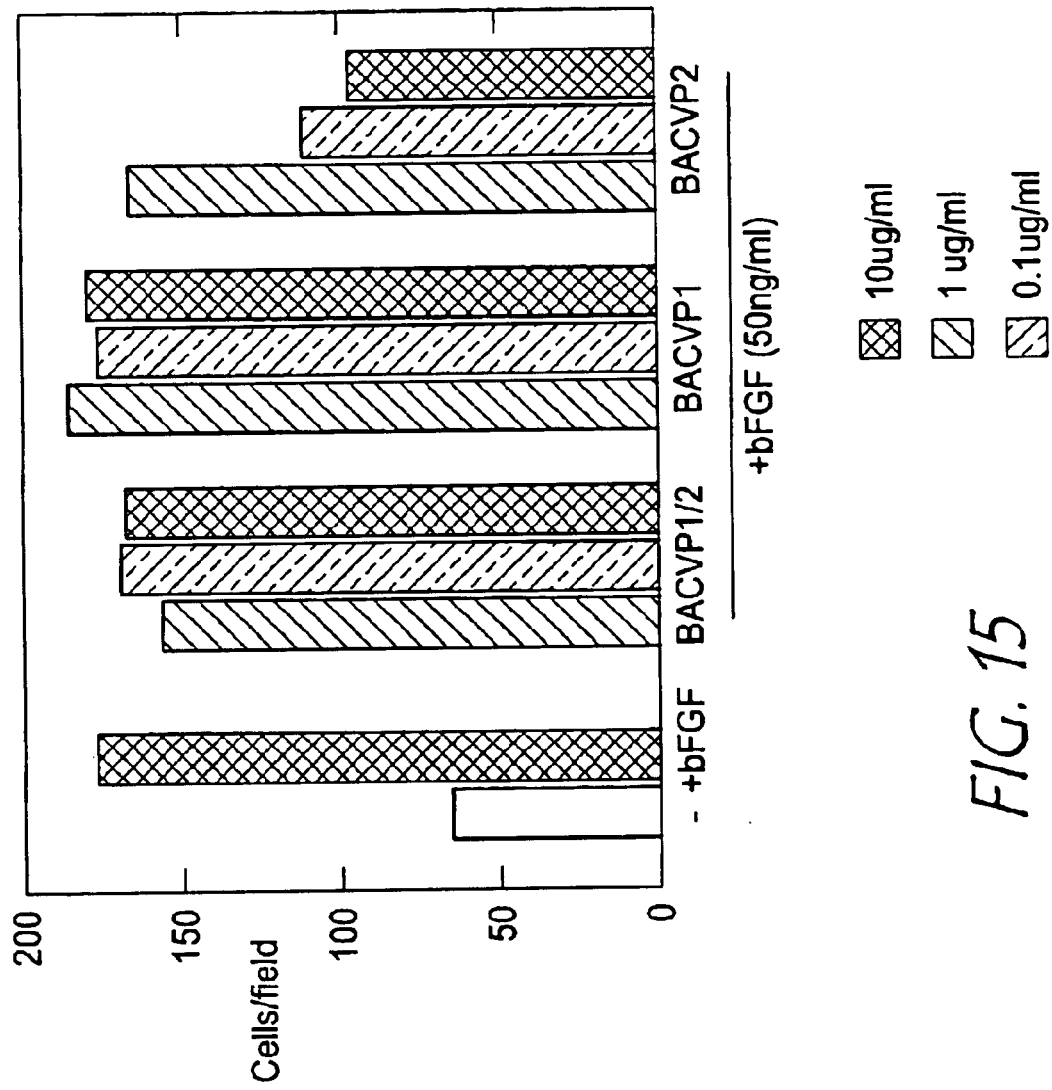

Overlapping peptides (20 mers) encompassing the entire B19 parvovirus VP2 protein (with a 10 amino acid overlap) were synthesized. These peptides were grouped into eight different pools (pools 1–7 containing 7 peptides and pool 8 containing 6 peptides) and each pool of peptides was tested for the ability to inhibit hematopoiesis and hematopoietic cell growth in colony formation assays. (See FIGS. 8A–H). In these experiments, the cells were incubated with various dilutions of the peptides prior to the 11-day colony formation assay. Each pool of peptides showed some degree of inhibition of colony formation and the peptides of pool 6 showed significant inhibition. (See FIG. 8F). The sequences of the peptides of each pool are provided in Table 6.

TABLE 6

VP2 peptide pools*

POOL 1
1 (position in protein)
MTSVNSAEASTGAGGGGSNP (SEQ ID NO.9)

TGAGGGGSNPVKSMWSEGAT (SEQ ID NO.10)

VKSMWSEGATFSANSVTCTF (SEQ ID NO.11)

FSANSVTCTFSRQFLIPYDP (SEQ ID NO.12)

TABLE 6-continued

VP2 peptide pools*

SRQFLIPYDPEHHYKVFSPA (SEQ ID NO.13)

EHHYKVFSPAASSCHNASGK (SEQ ID NO.14)

ASSCHNASGKEAKVCTISPI (SEQ ID NO.15)

POOL 2
71
EAKVCTISPIMGYSTPWRYL (SEQ ID NO.16)

MGYSTPWRYLDFNALNLFFS (SEQ ID NO.17)

DFNALNLFFSPLEFQHLIEN (SEQ ID NO.18)

PLEFQHLIENYGSIAPDALT (SEQ ID NO.19)

YGSIAPDALTVTISEIAVKD (SEQ ID NO.20)

VTISEIAVKDVTDKTGGGVQ (SEQ ID NO.21)

VTDKTGGGVQVTDSTTGRLC (SEQ ID NO.22)

POOL 3
141
VTDSTTGRLCMLVDHEYKYP (SEQ ID NO.23)

MLVDHEYKYPYVLGQGQDTL (SEQ ID NO.24)

YVLGQGQDTLAPELPIWVYF (SEQ ID NO.25)

APELPIWVYFPPQYAYLTVG (SEQ ID NO.26)

PPQYAYLTVGDVNTQGISGD (SEQ ID NO.27)

DVNTQGISGDSKKLASEESA (SEQ ID NO.28)

SKKLASEESAFYVLEHSSFQ (SEQ ID NO.29)

POOL 4
211
FYVLEHSSFQLLGTGGTATM (SEQ ID NO.30)

LLGTGGTATMSYKFPPVPPE (SEQ ID NO.31)

SYKFPPVPPENLEGCSQHFY (SEQ ID NO.32)

NLEGCSQHFYEMYNPLYGSR (SEQ ID NO.33)

EMYNPLYGSRLGVPDTLGGD (SEQ ID NO.34)

LGVPDTLGGDPKFRSLTHED (SEQ ID NO.35)

PKFRSLTHEDHAIQPQNFMP (SEQ ID NO.36)

POOL 5
281
HAIQPQNFMPGPLVNSVSTK (SEQ ID NO.37)

GPLVNSVSTKEGDSSNTGAG (SEQ ID NO.38)

EGDSSNTGAGKALTGLSTGT (SEQ ID NO.39)

KALTSLSTGTSQNTRISLRP (SEQ ID NO.40)

SQNTRISLRPGPVSQPYHHW (SEQ ID NO.41)

GPVSQPYHHWDTDKYVTGIN (SEQ ID NO.42)

DTDKYVTGINAISHGQTTYG (SEQ ID NO.43)

POOL 6
351
AISHGQTTYGNAEDKEYQQG (SEQ ID NO.44)

NAEDKEYQQGVGRFPNEKEQ (SEQ ID NO.45)

VGRFPNEKEQLKQLQGLNMH (SEQ ID NO.46)

TABLE 6-continued

VP2 peptide pools*

LKQLQGLNMHTYFPNKGTQQ (SEQ ID NO.47)

TYFPNKGTQQYTDQIERPLM (SEQ ID NO.48)

YTDQIERPLMVGSVWNRRAL (SEQ ID NO.49)

VGSVWNRRALHYESQLWSKI (SEQ ID NO.50)

POOL 7
421
HYESQLWSKIPNLDDSFKTQ (SEQ ID NO.51)

PNLDDSFKTQFAALGGWGLH (SEQ ID NO.52)

FAALGGWGLHQPPPQIFLKI (SEQ ID NO.53)

QPPPQIFLKILPQSGPIGGI (SEQ ID NO.54)

LPQSGPIGGIKSMGITTLVQ (SEQ ID NO.55)

KSMGITTLVQYAVGIMTVTM (SEQ ID NO.56)

YAVGIMTVTMTFKLGPRKAT (SEQ ID NO.57)

POOL 8
491
TFKLGPRKATGRWNPQPGVY (SEQ ID NO.58)

GRWNPQPGVYPPHAAGHLPY (SEQ ID NO.59)

PPHAAGHLPYVLYDPTATDA (SEQ ID NO.60)

VLYDPTATDAKQHHRHGYEK (SEQ ID NO.61)

KQHHRHGYEKPEELWTAKSR (SEQ ID NO.62)

PEELWTAKSRVHPL (SEQ ID NO.63)

*A total of 55 peptides (20 mers) having an overlap of 10 aminoacids were synthesized.
Protein product of nucleotides 3125–4889.See Shade, J Virol 58(3):921–36 (1986), herein expressly incorporated by reference in its entirety.

Additionally, peptides corresponding to regions of the B19 parvovirus VP2 capsid believed to be involved in binding to the P antigen were synthesised and analysed for their ability to inhibit hematopoiesis and the proliferation of hematopoietic cells. Chipman et al., *Proc Natl Acad Sci USA* 93:7502–7506 (1996), herein expressly incorporated by reference in its entirety. (See Table 7). Table 7 shows a deletion series of synthetic peptides that were screened to determine their ability to inhibit hematopoesis and cell growth. (See FIG. 9).

TABLE 7

| Deletion series of P antigen binding region of parvovirus B19 VP2 protein* | | |
|---|---|---|
| Peptide I: | GLNMHTYFPNKGTQQYTDQIE | (SEQ ID NO:2) |
| Peptide II: | TYFPNKGTQQYTDQIE | (SEQ ID NO:3) |
| Peptide III: | NKGTQQYTDQIE | (SEQ ID NO:4) |
| Peptide IV: | NKGTQQYTDQ | (SEQ ID NO:5) |
| Peptide V: | NKGTQQYT | (SEQ ID NO:6) |
| Peptide VI: | QQYTDQ | (SEQ ID NO:7) |

TABLE 7-continued

| Deletion series of P antigen binding region of parvovirus B19 VP2 protein* | | |
|---|---|---|
| Peptide VII: | QQYQ | (SEQ ID NO:8) |
| Peptide VIII: | QQY | |

*Peptide VII is not a deletion series peptide but rather an artificial sequence.

Among the peptides in Table 7, peptides IV-VIII showed good inhibition and the 3-mer (QQY) and the 10-mer (NKGTQQYTDQ SEQ ID NO. 5) were found to significantly inhibit hematopoiesis and cell growth. (See FIG. 9). Data are plotted in comparison with the medium control (the medium being 1.0) and represent one experiment in triplicate (mean+/−1 SD). As shown in FIG. 10, the 10-mer peptide showed significant inhibition of colony formation at about 1 to about 100 μM concentration. The next section describes the discovery that B19 parvovirus capsids can inhibit another type of cell that has a receptor that interacts with a parvovirus B19 capsid or fragment thereof—the endothelial cell.

B19 Parvovirus Capsids Inhibit the Growth of other Cells that Express a Receptor that Interacts with a Parvovirus B19 Capsid or Fragment thereof including, but not Limited to, Endothelial Cells The results from the experiments described in the preceding sections provide evidence that B19 parvovirus capsids, B19 parvovirus VP2 capsids, and fragments of B19 parvovirus VP2 capsids efficiently inhibit the growth of a number of different hematopoietic cells that have a receptor that interacts with a parvovirus B19 capsid or fragment thereof (e.g., a P antigen containing cell), including hematopoietic cells from different species. In a another set of experiments, it was discovered that recombinant B19 parvovirus capsids inhibit the growth of endothelial cells, as evidenced by a reduction in endothelial cell proliferation and migration. A description of these experiments is provided below.

To determine whether B19 parvovirus capsids can inhibit endothelial cell proliferation, assays were performed in which primary human umbilical vein endothelial cells, plated at a density of $1.5\times10^4$ cells per well in a 24 well plate, were incubated with B19 parvovirus capsids in the presence of 0.5% fetal calf serum+10.0 ng/ml basic fibroblast growth factor. The various B19 parvovirus capsid preparations (i.e., VP1/2 or capsids made with only VP1 or VP2) were added to each well on the following day and the cells with capsids were incubated for additional 72 hours. Cell proliferation was then determined by using a crystal violet dye assay. Accordingly, capsid treated cells were washed in PBS, fixed in 3.7% formaldehyde, and incubated with crystal violet. The dye was then removed by extensive washes with distilled water. The cell-associated crystal violet was solubilized with 10% acetic acid and quantified at absorbance 540 nm in an ELISA plate reader.

FIGS. 11–14 show the results of several endothelial cell proliferation assays, wherein the "x axis" displays an increasing concentration of control antigen KYVTGIN (SEQ. ID. NO. 1) (FIG. 11), B19 parvovirus capsid (VP1 alone) (FIG. 12), B19 parvovirus capsid (VP1/2) FIG. 13), and B19 parvovirus capsid (VP2 alone) (FIG. 14). Thus, from left to right, the bars represent the absorbance at 540 nm with 0 $\mu$g/ml, 0.01 $\mu$g/ml, 0.1 $\mu$g/ml, 1.0 $\mu$g/ml, and 10.0 $\mu$g/ml. The "y axis" shows a standard of absorbance values at 540 nm. The standard deviation was within 10%. As shown in FIG. 14, VP2 capsids efficiently inhibit endothelial cell proliferation at concentrations as low as 1.0 $\mu$g/ml and significant inhibition was observed at 10.0 $\mu$g/ml.

The effect of B19 parvovirus capsid preparations on cell migration was also determined. The migration assays were performed using a modified Boyden chamber assay (Neuroprobe, Inc.). Basic fibroblast growth factor (40 ng/ml) was added to stimulate migration of the HUVEC cells through a collagen 1 coated 8 $\mu$m pore size millipore filter. Cells were incubated for 60 min with the various B19 parvovirus capsid preparations (i.e., VP1/2 or capsids made with only VP1 or VP2) prior to conducting the migration assay. To perform the migration assay, the Boyden chamber was incubated for 4.5 h at 37° C. in a 10% $CO_2$ atmosphere. The filters were subsequently removed and were fixed in 3.7% formaldehyde. Cell migration was visualized by staining the filters overnight in Gill's Hematoxylin. The number of migrating cells were scored by counting stained cells on the migrating side of the filter per high power magnification field. (See FIG. 15). As shown in FIG. 15, VP2 capsids at concentrations as low as 1 $\mu$g/ml effectively inhibited endothelial cell migration. Further, the VP2 capsid-mediated inhibition of endothelial cell migration was significantly more potent than that observed with either native capsids (VP1/2) or capsids having only VP1.

It should be understood that the optimal candidate molecules for the inhibition of hematopoiesis and cell growth or migration may not be molecules that completely or even significantly inhibit hematopoiesis and/or cell growth or migration because complete or significant inhibition may have unwanted side effects for a patient, for example. In many cases, molecules that only reduce or compromise hematopoiesis, cell proliferation, or migration may be desired. Accordingly, molecules identified herein as having any capacity to reduce or inhibit cell growth or migration are of significant therapeutic value. As will be discussed in greater detail below, techniques in protein engineering, computer modeling, epitope mapping, and the "capsid agent characterization assays" described herein, can be employed to rapidly manufacture and identify peptides of varying capacity to inhibit hematopoiesis, cell growth, and cell migration.

The term "capsid agent characterization assays" is intended to mean assays that analyze the ability of a "capsid agent" to inhibit the growth of a cell that has the P antigen. Examples of capsid agents include, but are not limited to, a B19 parvovirus VLP or a VP1/2, or VP1 or VP2 capsid or modified or unmodified peptide fragments of VP1 or VP2 or both or synthetic molecules having sequences of VP1 or VP2 or both or peptidomimetics that resemble VP1 or VP2 or regions of either or both of these molecules. Examples of capsid agent characterization assays include, but are not limited to, colony formation assays, neutralization assays, protein binding or fusion assays, internalization assays, transcription or translation assays, and assays that evaluate the phosphorylation of proteins or calcium mobilization in a cell after contact with a capsid agent. (See also U.S. Pat. No. 5,508,186 to Young et aL, which describes several capsid agent characterization assays). The section below teaches the manufacture and characterization of more capsid agents that inhibit cell growth and cell migration.

B19 Parvovirus Capsid Agents that Inhibit Growth and Migration of Cells that have a Receptor that Interacts with a Parvovirus B19 Capsid or Fragment thereof (e.g., a P Antigen Containing Cell)

This section describes several techniques that can be used to manufacture, design, and characterize capsid agents, including but not limited to, B19 parvovirus capsids, modified B19 parvovirus capsids, B19 parvovirus VP2 capsids, fragments of these molecules, and peptidomimetics that resemble these structures. The VP1 and VP2 structural gene has been sequenced in its entirety and this sequence can be obtained from the NCBI database source accession number U38506.1, or accession number AAB47788, or medline number 97081188, or as published by Erdman et al., *J. Gen. Virol.,* 77: 2767 (1996), all references and sequences therein are hereby expressly incorporated by reference. The VP1 or VP2 or fragments of either or both used with embodiments of the invention correspond to sequences involved in the inhibition of cell growth and cell migration. Desirable peptides consist, consist essentially of, or comprise between three amino acids and 780 amino acids of the VP1 and VP2 structural protein but have at least some portion of the molecule that is involved in the inhibition of growth and/or migration of cells that have a receptor that interacts with a parvovirus B19 capsid or fragment thereof (e.g., a P antigen containing cell). In other words, preferable embodiments of the invention concern at least three amino acids, four amino acids, five amino acids, six amino acids, seven amino acids, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirtysix, thirty-seven, thirty-eight, thirty nine, or forty or fifty or sixty or seventy or eighty or ninety or one-hundred amino acids of either the VP1 or the VP2 structural gene or both. Desirable embodiments concern at least 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, or 780 amino acids of the VP1 or VP2 structural protein or both.

The peptides and fragments or derivatives thereof that are involved in the inhibition of growth and migration of cells that have the P antigen, include but are not limited to, those regions of the VP1 and VP2 structural gene that is found in nature. Additionally, altered sequences in which functionally equivalent amino acid residues are substituted for residues within the sequence resulting in a silent change can also be present in these capsid agents. In some aspects of the invention, the term "consisting essentially of" encompasses the molecules described above because the changes made to the capid agents are not material alterations. That is, one or more amino acid residues within the sequence of the VP1 or VP2 structural gene, or a fragment thereof can be substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The uncharged polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic aminoacids include phenylalanine, tryptophan, and tyrosine. The peptides described above are preferably analyzed in assays to determine whether the fragment has retained the ability to inhibit the growth and/or migration of cells that have a receptor that interacts with a parvovirus B19 capsid or fragment thereof (e.g., a P antigen containing cell).

Peptides for use in aspects of the invention can also be modified, e.g., the peptides can have substituents not normally found on a peptide or the peptides can have substituents that are normally found on the peptide but are incorporated at regions of the peptide that are not normal. These peptides can be acetylated, acylated, or aminated, for example. Substituents that can be included on the peptide so as to modify it include, but are not limited to, H, alkyl, aryl, alkenyl, alkynl, aromatic, ether, ester, unsubstituted or substituted amine, amide, halogen or unsubstituted or substituted sulfonyl or a 5 or 6 member aliphatic or aromatic ring. The fragments described herein, for example, can have a carboxy terminal amide or can have one or more D amino acids or can be retroinverso peptides. In some embodiments, the term "consisting essentially of" encompasses the modified capsid agents above.

Additionally, VP1 or VP2 or fragments of either or both can be derivatized in that the derivative polypeptide can be manipulated to include amino acid sequences that effect the function and stability of the molecule. For example, peptides that are involved in the inhibition of growth and migration of cells that have the P antigen can be engineered to have one or more cysteine residues so as to promote the formation of a more stable derivative through disulfide bond formation. (See e.g., U.S. Pat. No. 4,908,773). Computer graphics programs and the assays described herein can be employed to identify cystine linkage sites that provide greater stability but do not perturb the ability to inhibit growth or migration of cells that have a receptor that interacts with a parvovirus B19 capsid or fragment thereof (e.g., a P antigen containing cell). (See e.g., Perry, L. J., & Wetzel, R., *Science*, 226:555–557 (1984); Pabo, C. O., et al., *Biochemistry*, 25:5987–5991 (1986); Bott, R., et al., European Patent Application Ser. No. 130,756; Perry, L. J., & Wetzel, R., *Biochemistry*, 25:733–739 (1986); Wetzel, R. B., European Patent Application Ser. No. 155,832).

Additional derivatives that are embodiments of the invention include peptidomimetics that resemble regions of VP1, VP2, or both. Synthetic peptides can be prepared that correspond to these molecules by employing conventional synthetic methods, utilizing L-amino acids, D-amino acids, or various combinations of amino acids of the two different configurations. Synthetic compounds that mimic the conformation and desirable features of a particular peptide but avoid the undesirable features, e.g., flexibility (loss of conformation) and bond breakdown are known as "peptidomimetics". (See, e.g., Spatola, A. F. Chemistry and Biochemistry of Amino Acids. Peptides, and Proteins (Weistein, B, Ed.), Vol. 7, pp. 267–357, Marcel Dekker, New York (1983), which describes the use of the methylenethio bioisostere [$CH_2$ S] as an amide replacement in enkephalin analogues; and Szelke et al., In peptides: Structure and Function, Proceedings of the Eighth American Peptide Symposium, (Hruby and Rich, Eds.); pp. 579–582, Pierce Chemical Co., Rockford, Ill. (1983), which describes renin inhibitors having both the methyleneamino [$CH_2$ NH] and hydroxyethylene [$CHOHCH_2$] bioisosteres at the Leu-Val amide bond in the 6–13 octapeptide derived from angiotensinogen). Numerous methods and techniques are known in the art for designing and manufacturing peptidomimetcs, any of which could be used. (See, e.g., Farmer, P. S., Drug Design, (Ariens, E. J. ed.), Vol. 10, pp. 119–143 (Academic Press, New York, London, Toronto, Sydney and San Francisco) (1980); Farmer, et al., in TIPS, 9/82, pp. 362–365; Verber et al., in TINS, 9/85, pp. 392–396; Kaltenbronn et al., in J. Med. Chem. 33: 838–845 (1990); and Spatola, A. F., in Chemistry and Biochemistry of Amino Acids. Peptides, and Proteins, Vol. 7, pp. 267–357, Chapter 5, "Peptide Backbone Modifications: A Structure-Activity Analysis of Peptides Containing Amide Bond Surrogates. Conformational Constraints, and Relations" (B. Weisten, ed.; Marcell Dekker: New York, pub.) (1983); Kemp, D. S., "Peptidomimetics and the Template Approach to Nucleation of beta.-sheets and alpha.-helices in Peptides," Tibech, Vol. 8, pp. 249–255 (1990). Additional teachings can be found in U.S. Pat. Nos. 5,288,707; 5,552,534; 5,811,515; 5,817,626; 5,817,879; 5,821,231; and 5,874,529, herein incorporated by reference. Accordingly, peptidomimetics of the invention can have structures that resemble between at least 3 and 780 amino acids. That is, they can resemble 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, or 780 amino acids of the VP1 or VP2 structural protein so long as some region of the molecule inhibits the growth or migration of a cell that has a receptor that interacts with a parvovirus B19 capsid or fragment thereof (e.g., a P antigen containing cell).

Conventional techniques in molecular biology, such as those described in U.S. Pat. No. 5,508,186, herein expressly incorporated by reference in its entirety, can be used to prepare numerous types of capsid agents. The term "capsid agents" can refer to capsids comprising VP1, VP2, VP1/2 in varying proportions, fragments of VP1 or VP2 or either or both, fusion proteins having sequences that correspond to VP1 or VP2 or both, and modified or unmodified proteins or peptides or peptidomimetics that correspond to sequences of the VP1 and VP2 structural gene that are involved in the inhibition of growth and/or migration of cells that have a receptor that interacts with a parvovirus B19 capsid or fragment thereof (e.g., a P antigen containing cell).

By the approach described in U.S. Pat. No. 5,508,186 a capsid agent can be manufactured as follows. Plasmids can be constructed to contain either full length VP1 or VP2 or both. To construct plasmid pVP1/941, a cDNA encoding the VP1 gene can be excised from pYT103c, a nearly full length molecular clone of B19 parvovirus (Cotmore et al. Science 226:1161 (1984); Ozawa et al. J. Virol. 62:2884 )1988)), by digestion with the restriction enzymes Hind III (which cuts at map unit 45) and EcoRI (which cuts at map unit 95) followed by treatment with mung bean nuclease to complement single stranded ends. The resultant DNA fragment is then inserted into the BamHI site (made blunt ended with the Klenow fragment of DNA polymerase) of the baculovirus transfer vector pVL941, a vector derived by deletion of the polyhedrin gene of AcMNPV (*Autographa california* nuclear polyhedrosis virus) followed by cloning into the pUC8 plasmid (Summers et al. Tex. Agric. Exp. Stn. 1555 (1987)). Construction of pVP2/941 is performed by the insertion of a PstI-EcoRI digestion fragment of pYT103c (map units 58–95; the EcoRI site was blunt-ended) and a synthetic DNA fragment of 20 nucleotides corresponding to the SstI-PstI region (again with the SstI site blunt-ended) into the BamHI site of pVL941. Additionally, the Polymerase Chain Reaction (PCR) can be used to clone the VP1 or VP2 gene or portions thereof from full-length clones as described by Erdman et al., *J. Gen Virol.* 77:2767 (1996), herein incorporated by reference in its entirety. To facilitate cloning, the primers can be designed to generate convenient sites for restriction digestion, as is known in the art.

Recombinant plasmids encoding VP1, VP2, VP1/2, or fragments thereof are then transfected into insect cells to generate recombinant baculoviruses. Accordingly, 8 $\mu$g of the recombinant plasmid is cotransfected into Sf9 cells with 2 $\mu$g of wild type AcMNPV, using calcium phosphate-mediated precipitation. The Sf9 cell line (American Type Culture Collection, Rockville Md.), which is derived from *Spodoptera frugiperda* (fall army worm) ovary, is maintained in Grace's insect tissue culture medium containing 10% heat inactivated fetal bovine serum, 2.5 $\mu$g/ml fungizone, 50 $\mu$/ml gentamicin, 3.33 mg/ml lactalbumin hydrolysate, and 3.33 mg/ml yeastolate (provided complete by Gibco BRL Life Technologies, Gaithersburg Md.) at 100% room air, 95% humidity, at 27° C. Six days after transfection, progeny virus is harvested and replaqued onto fresh Sf9 cells. Recombinant viruses are recognized visually by the absence of occlusion bodies in the nucleus of cells (the occlusion-positive phenotype is the result of synthesis of large quantities of the polyhedrin protein). Recombinant viruses can be subjected to three cycles of plaque purification before large scale VLP stocks are prepared and isolated or purified. Purified compositions containing 0.1%, 0.5%, 1%, 2%, 5%, 10%, 25%, or more (weight/weight) of the active ingredient are specifically contemplated.

The term "isolated" requires that the material be removed from its original environment (e.g., the natural environment if it is naturally occurring). For example, a naturally occurring protein present in a living cell is not isolated, but the same protein, separated from some or all of the coexisting materials in the natural system, is isolated. The term "purified" does not require absolute purity; rather it is intended as a relative definition. For example, proteins are routinely purified to electrophoretic homogeneity, as detected by Coomassie staining, and are suitable in several assays despite having the presence of contaminants. Preferably, capsid agent characterization assays are performed on the isolated or purified capsid agents including, but not limited to, the assays described in U.S. Pat. No. 5,508,186 (e.g., DNA, RNA, and proten analysis, immunoblots, immunofluorescence, sedimentation analysis, electron microscopy, immune electron microscopy, and the capsid agent characterization assays described previously.

In some embodiments, particularly for applications that involve the long-term administration of capsid agents, it is desirable to manufacture a pharmaceutical that does not elicit a significant immune response in a subject. A general scheme for the manufacture of capsid agents that do not induce an immune response involves design of the agent, construction of the agent, analysis of the agent's ability to inhibit cell growth and/or cell migration and an analysis of the immune response generated to the agent. Many of the immunogenic regions of the B19 parvovirus capsid are known and, through conventional techniques in molecular biology, these immunogenic regions can be deleted, mutagenized, or modified and the newly designed synthetic capsid proteins can be analyzed in one or more capsid agent characterization assays (e.g., a colony formation assay and a neutralization assay using sera generated from asymptomatic individuals). Many methods can be employed to identify the immunogenic regions of the B19 parvovirus capsid and manufacture non-immunogenic VLPs that inhibit cell growth and/or migration and the example below is provided as one possible approach.

Test expression constructs can be designed, manufactured, and analyzed as follows. This process can be iterative so as to generate several classes of VLPs and pharmaceuticals having these capsid agents, which differ according to their ability to inhibit cell growth, cell migration, and induce an immune response in a subject. Accordingly, by one approach, the VP2 structural gene can be cloned from clinical isolates using PCR with primers designed from the published VP2 sequence. The VP2 gene is subsequently subcloned both into BlueScript (Pharmacia) for mutagenesis, and pVL1393 (Stratagene) for expression in Sf9 cells. Mutations that correspond to immunogenic regions of VP2 (e.g., amino acids 253–272, 309–330, 328–344, 359–382, 449–468, and 491–515) are introduced into the VP2 gene using Amersham Sculptor in vitro mutagenesis kit. One of skill in the art will appreciate that carboxy truncations, amino truncations, internal truncations, and site-directed mutagenesis of the VP1 and VP2 structural protein can be accomplished by several approaches. Preferably, several different clones having one or more of the deletions described above are generated. The appearance of a desired mutation is confirmed by sequencing and the mutated gene is then subcloned into pVL1393 for expression in Sf9 cells. The SF9 cells are then transfected using BaculoGold Transfection kit (Pharmingen). Transfections can be performed according to the manufacturer's instructions with the following modifications. Approximately, $8 \times 10^8$ Sf9 cells are transfected in a 100 mM dish, with 4 $\mu$g of BaculoGold DNA and 6 $\mu$g of test DNA. Cells are harvested after 6 days and assayed for VLP production.

Next, cells are harvested by scraping followed by low speed centrifugation. Cells are then resuspended in 300 ml of breaking buffer (1 M NaCl, 0.2 M Tris pH 7.6) and homogenized for 30 seconds on ice using a Polytron PT 1200 B with a PT-DA 1205/2-A probe (Brinkman) in a Falcon 1259 tube. Samples are spun at 2500 rpm for 3 minutes to pellet debris and the tubes are washed with an additional 150 ml of breaking buffer. The supernatants are collected in a 1.5 ml microfuge tubes and are re-spun for 5 minutes in an Eppendorf microfuge (Brinkman). The collected supernatants can be stored at 4° C.

ELISA assays can then be performed on the isolated VLPs as follows. Approximately, 5 ml of extract is diluted into 50 ml of 1% BSA in PBS (phosphate buffered saline; 20 mM $NaPO_4$, pH 7.0, 150 mM NaCl) and is plated onto a polystyrene plate. The plate is incubated overnight at 4° C. Extracts are removed and the plate is blocked with 5% powdered milk in PBS. All subsequent wash steps are performed with 1% BSA in PBS. The plate is incubated at room temperature with primary antibody for 1 hour (e.g., sera generated from asymptomatic individuals). After washing to remove unbound antibody, plates are incubated for 1 hour with secondary antibody. The secondary antibody, peroxidase labeled Goat anti-Mouse IgG (g), can be purchased from Kirkegaard & Perry Laboratories, Inc. and can be used at $10^3$ dilution in 1% BSA in PBS. After a final washing, an alkaline phosphatase assay is performed and absorbance is read at 405 nm. The most successful capsid agents by this assay will be ones that evade detection. That is, desired mutant VP2 capsids are ones that have lost epitopes recognized by antibodies present in the sera and, thus, are not detected by the ELISA. By performing these experiments with several lots of sera obtained from different individuals and the monoclonal antibodies that neutralize the inhibition of colony formation or cell migration, one of skill can rapidly identify the regions of VP2 that are immunogenic and mutant VP2 capsids that best evade an immune response.

Next, the mutant VP2 capsids that successfully evade detection by the ELISA method described above are analyzed for their ability to inhibit cell growth and cell migration by using a capsid agent characterization assays. By assessing each mutant VP2 capsid's ability to inhibit cell growth and cell migration and coordinating this information with the immunogenicity results from the ELISA analysis, "a capsid agent profile" can be generated. A "capsid agent profile" can include a symbol or icon that represents a mutant capsid protein or mutant VLP, sequence information (e.g., the location of mutations or modifications), a capsid agent class designation (e.g., information regarding relationships to other capsid agents), application information (e.g., disease indications or treatment information, or clinical or biotechnological uses), and performance information from capsid agent characterization assays (e.g., values obtained from the colony formation assays, neutralization assays, fusion/internalization assays, binding assays, phosphorylation assays, cell migration assays, proliferation assays, and results obtained from immunogenicity analysis including the ELISA assays).

Capsid agent profiles can be recorded on a computer readable media, stored in a database, on hardware, software, or memory, accessed with a search engine and can be compared with one another or associated with a disease state or "disease state profile", which is information relating to a disease, condition or indicated treatment. These capsid agent profiles and disease state profiles can be used by investigators for rational drug design or biochemical analysis or by physicians or clinicians who wish to choose an appropriate pharmaceutical composition that balances the optimal level of cell growth and cell migration inhibition with immune response of the subject in light of the desired duration of treatment.

In several embodiments, the capsid agents are disposed on a support so as to create a multimeric capsid agent. While a monomeric agent (that is, an agent that presents a discrete molecule, thus, carrying only one binding domain) can be sufficient to achieve a desired response, a multimeric agent (that is, an agent that presents multiple molecules, thus, having several domains) often times can elicit a greater response. It should be noted that the term "multimeric" refers to the presence of more than one molecule on a support, for example, several individual molecules of B19 parvovirus VP2 capsid joined to a support, as distinguished from the term "multimerized" that refers to an agent that has more than one molecule joined as a single discrete compound molecule on a support, for example several molecules of B19 parvovirus VP2 capsid joined to form a single compound molecule that is joined to a support. A multimeric form of the capsid agents described herein can be advantageous for many biotechnological or clinical applications because of the ability to obtain an agent with higher affinity for a cell having a receptor that interacts with a parvovirus B19 capsid or fragment thereof (e.g., a P antigen containing cell).

A multimeric capsid agent can be obtained by coupling the protein, for example, B19 parvovirus VP2 capsid or a fragment thereof to a macromolecular support. A "support" may also be termed a carrier, a resin or any macromolecular structure used to attach or immobilize a protein. The macromolecular support can have a hydrophobic surface that interacts with regions of the capsid agent by hydrophobic non-covalent interactions. The hydrophobic surface of the support can be, for example, a polymer such as plastic or any other polymer in which hydrophobic groups have been linked such as polystyrene, polyethylene, PTFE, or polyvinyl. Alternatively, capsid agents can be covalently bound to carriers including proteins and oligo/polysaccharides (e.g. cellulose, starch, glycogen, chitosane or aminated sepharose). In these later embodiments, a reactive group on capsid agent, such as a hydroxy or the amino present in the peptide, can be used to join to a reactive group on the carrier so as to create the covalent bond. Embodiments also can comprise a support with a charged surface that interacts with the capsid agent. Additional embodiments concern a support that has other reactive groups that are chemically activated so as to attach a capsid agent. For example, cyanogen bromide activated matrices, epoxy activated matrices, thio and thiopropyl gels, nitrophenyl chloroformate and N-hydroxy succinimide chlorformate linkages, or oxirane acrylic supports can be used. (SIGMA).

Further, the support can comprise inorganic carriers such as silicon oxide material (e.g. silica gel, zeolite, diatomaceous earth or aminated glass) to which the capsid agent is covalently linked through a hydroxy, carboxy or amino group of the peptide and a reactive group on the carrier. Thus, in appropriate contexts, a "support" can refer to the walls or wells of a reaction tray, test tubes, catheters, stents, balloons, prosthetics, medical devices, polystyrene beads, magnetic beads, nitrocellulose strips, membranes, microparticles such as latex particles, sheep (or other animal) red blood cells, Duracyte® artificial cells, and others. Inorganic carriers, such as silicon oxide material (e.g. silica gel, zeolite, diatomaceous earth or aminated glass) to which the capsid agents are covalently linked through a hydroxy, carboxy or amino group and a reactive group on the carrier are also embodiments. Carriers for use in the body, (e.g., for prophylactic or therapeutic applications) are preferably physiological, non-toxic and non-immunoresponsive. Such carriers include, but are not limited to, poly-L-lysine, poly-D, L-alanine and Chromosorb® (Johns-Manville Products, Denver, Colo.).

In other embodiments, linkers, such as λ linkers or biotin-avidin (or streptavidin), of an appropriate length are inserted between the capsid agent and the support so as to encourage greater flexibility and thereby overcome any steric hindrance that is presented by the support. The determination of an appropriate length of linker that allows for optimal interaction is made by screening the capsid agents having varying length linkers in the capsid agent characterization assays described herein.

In other embodiments, the multimeric supports discussed above have attached multimerized capsid agents so as to create a"multimerized-multimeric support". An embodiment of a multimerized capsid agent is obtained by creating an expression construct having two or more nucleotide sequences encoding VP2 or a fragment thereof, for example, joined together. The expressed fusion protein is one embodiment of a multimerized capsid agent and is then joined to a support. A support having many such multimerized agents is termed a multimerized-multimeric support. Linkers or spacers between the domains that make-up the multimerized agent and the support can be incorporated for some embodiments and optimally spaced linkers can be determined using the capsid agent characterization assays.

In some embodiments, capsid agents are disposed on prosthetic devices that are implanted into a subject. With many types of prosthetics, for example, stents and valves, a limited amount of tissue ingrowth is desired so as to stabilize the implant. During implantation, however, the injury to surrounding tissue results in a considerable increase in cellular proliferation, which can cause fibrotic build up or restenosis and, over time, constriction of a stent or repositioning of a valve. Prior art devices have sought to overcome this problem through the use of radioactivity, however, the treatment success and potential for systemic exposure to the radioactive substances that are released from the device makes such approaches less than desirable. Similarly, oftentimes techniques such as balloon angioplasty result in restenosis caused by the infiltration of endothelial cells.

By attaching capsid agents to medical prosthetics, such as stents or valves, or delivering capsid agents through porous catheters (e.g., balloon cathers as used in angioplasty) endothelial cell migration, proliferation, fibrotic build up, tissue ingrowth, and restenosis can be efficiently inhibited. Further, a delayed tissue ingrowth can be obtained by using capsid agents that are cleared by the immune system at a time after the inflammation associated with the medical procedure has quelled. By using the approaches described above, capsid agents can be attached to many different types of prosthetics, e.g., stents or valves, through hydrophobic interactions or covalent linkages. Further, cathers in the prior art can be adapted for the delivery of capsid agents to the site of angioplasty. By analyzing the capsid agent profiles, a physician can select the appropriate capsid agent-coated prosthetic for implantation or the appropriate capsid agent for delivery depending on the desired time of cell inhibition or delay in tissue ingrowth. Localized delivery of capsid agents in other manners is also contemplated. Thus, for example, growth of vascular endothelial cells can be inhibited by implanting a controlled release composition in the vicinity of a stent, graft, valve, or other prosthetic, or by delivering the drug to the site via infusion pump or other suitable device. In addition to coatings for medical devices and formulations for catheter delivery, the capsid agents described herein can be formulated in pharmaceuticals and used to treat or prevent human diseases or conditions associated with proliferation or migration of cells that have the P antigen. The section below discusses the many ways to formulate capsid agents into pharmaceuticals and determine an appropriate dose.

The Manufacture and Dose of Therapeutic and Prophylactic Agents

The capsid agents of the invention (e.g., B19 parvovirus VP1, VP1/2, VP2 capsids or fragments thereof) are suitable for treatment of subjects either as a preventive measure to avoid a disease or condition, or as a therapeutic to treat subjects already afflicted with a disease. These pharmacologically active compounds can be processed in accordance with conventional methods of galenic pharmacy to produce medicinal agents for administration to subjects, e.g., mammals including humans. The active ingredients can be incorporated into a pharmaceutical product with and without modification. Further, the manufacture of pharmaceuticals or therapeutic agents that deliver the pharmacologically active compounds described herein by several routes are aspects of the invention. For example, and not by way of limitation, DNA, RNA, and viral vectors having sequences encoding the capsid agents are used with embodiments. Nucleic acids encoding capsid agents can be administered alone or in combination with other active ingredients.

The compounds of this invention can be employed in admixture with conventional excipients, i.e., pharmaceutically acceptable organic or inorganic carrier substances suitable for parenteral, enteral (e.g., oral) or topical application that do not deleteriously react with the pharmacologically active ingredients of this invention. Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. Many more suitable vehicles are described in *Remmington's* Pharmaceutical Sciences, 15th Edition, Easton:Mack Publishing Company, pages 1405–1412 and 1461–1487 (1975) and The National *Formulary* XIV, 14th Edition, Washington, American Pharmaceutical Association (1975), herein incorporated by reference. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The effective dose and method of administration of a particular pharmaceutical formulation can vary based on the individual patient and the type and stage of the disease, as well as other factors known to those of skill in the art. Therapeutic efficacy and toxicity of such compounds can be determined by standard pharmaceutical procedures in cell cultures or experimental animals, e.g., ED50 (the dose therapeutically effective in 50% of the population). Any monkey species with a receptor which makes them permissive to the B19 capsid effect are appropriate experimental models, as described earlier. The data obtained from cell culture assays and animal studies is used in formulating a range of dosage for human use. The dosage of such compounds lies preferably within a range of circulating concentrations that include the ED50 with no toxicity. The dosage varies within this range depending upon type of capsid agent, the dosage form employed, sensitivity of the patient, and the route of administration.

Normal dosage amounts may vary from approximately 1 to 100,000 micrograms, up to a total dose of about 10 grams, depending upon the route of administration. Desirable dosages include 250 µg, 500 µg, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5, 6 g, 7 g, 8 g, 9 g, and 10 g. Additionally, the conentration of the capsid agents can be quite high in embodiments that administer the agents in a topical form. Molar concentrations of capsid agents can be used with some embodiments. Desirable concentrations for topical administration and/or for coating medical equipment range from 100 μM to 800 mM. Preferable concentrations for these embodiments range from 500 μM to 500 mM. For example, preferred concentrations for use in topical applications and/or for coating medical equipment include 500 μM, 550 μM, 600 μM, 650 μM, 700 μM, 750 μM, 800 μM, 850 μM, 900 μM, 1 mM, 5 mM, 10 mM, 15 mM, 20 mM, 25 mM, 30 mM, 35 mM, 40 mM, 45 mM, 50 mM, 60 mM, 70 mM, 80 mM, 90 mM, 100 mM, 120 mM, 130 mM, 140 mM, 150 mM, 160 mM, 170 mM, 180 mM, 190 mM, 200 mM, 300 mM, 325 mM, 350 mM, 375 mM, 400 mM, 425 mM, 450 mM, 475 mM, and 500 mM.

In some embodiments, the dose of capsid agent preferably produces a tissue or blood concentration or both from approximately 0.1 μM to 500 mM. Desirable doses produce a tissue or blood concentration or both of about 1 to 800 μM. Preferable doses produce a tissue or blood concentration of greater than about 10 μM to about 500 μM. Preferable doses are, for example, the amount of capsid agent required to achieve a tissue or blood concentration or both of 10 μM, 15 μM, 20 μM, 25 μM, 30 μM, 35 μM, 40 μM, 45 μM, 50 μM, 55 μM, 60 μM, 65 μM, 70 μM, 75 μM, 80 μM, 85 μM, 90 μM, 95 μM, 100 μM, 110 μM, 120 μM, 130 μM, 140 μM, 145 μM, 150 μM, 160 μM, 170 μM, 180 μM, 190 μM, 200 μM, 220 μM, 240 μM, 250 μM, 260 μM, 280 μM, 300 μM, 320 μM, 340 μM, 360 μM, 380 μM, 400 μM, 420 μM, 440 μM, 460 μM, 480 μM, and 500 μM. Although doses that produce a tissue concentration of greater than 800 μM are not preferred, they can be used with some embodiments of the invention. A constant infusion of the capsid agent can also be provided so as to maintain a stable concentration in the tissues as measured by blood levels.

The exact dosage is chosen by the individual physician in view of the patient to be treated. Dosage and administration are adjusted to provide sufficient levels of the active moiety or to maintain the desired effect. Additional factors that can be taken into account include the severity of the disease state of the patient, age, and weight of the patient; diet, time and frequency of administration, drug combination(s), reaction sensitivities, and tolerance/response to therapy. Short acting pharmaceutical compositions can be administered daily whereas long acting pharmaceutical compositions can be administered every 2, 3 to 4 days, every week, or once every two weeks. It is also contemplated that short acting compositions could have long term effects in that the compositions may have an immediate effect on hematopoiesis that takes the body several days or weeks to recover. Depending on half-life, clearance rate of the particular formulation, and the time takes an individual to recover from the inhibition of hematopoiesis, for example, the pharmaceutical compositions of the invention can be administered once, twice, three, four, five, six, seven, eight, nine, ten or more times per day, week, or month.

Routes of administration of the pharmaceuticals of the invention include, but are not limited to, transdermal, parenteral, gastrointestinal, transbronchial, and transalveolar. Transdermal administration is accomplished by application of a cream, rinse, gel, etc. capable of allowing the pharmacologically active compounds to penetrate the skin. Parenteral routes of administration include, but are not limited to, electrical or direct injection such as direct injection into a central venous line, intravenous, intramuscular, intraperitoneal, intradermal, or subcutaneous injection. Gastrointestinal routes of administration include, but are not limited to, ingestion and rectal. Transbronchial and transalveolar routes of administration include, but are not limited to, inhalation, either via the mouth or intranasally.

Compositions having the pharmacologically active compounds of this invention that are suitable for transdermal administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al., herein incorporated by reference.

Compositions having the pharmacologically active compounds of this invention that are suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, intradermal, or subcutaneous injection.

Compositions having the pharmacologically active compounds of this invention that are suitable for transbronchial and transalveolar administration include, but not limited to, various types of aerosols for inhalation. Devices suitable for transbronchial and transalveolar administration of these are also embodiments. Such devices include, but are not limited to, atomizers and vaporizers. Many forms of currently available atomizers and vaporizers can be readily adapted to deliver compositions having the pharmacologically active compounds of the invention.

Compositions having the pharmacologically active compounds of this invention that are suitable for gastrointestinal administration include, but not limited to, pharmaceutically acceptable powders, pills or liquids for ingestion and suppositories for rectal administration. Due to the ease of use, gastrointestinal administration, particularly oral, is a preferred embodiment. Once the pharmaceutical comprising the capsid agent has been obtained, it can be administered to a subject in need to treat or prevent diseases or conditions associated with proliferation or migration of a cell that has a receptor that interacts with a parvovirus B19 capsid or fragment thereof (e.g., a P antigen containing cell).

Aspects of the invention also include a coating for medical equipment such as prosthetics, implants, and instruments. Coatings suitable for use in medical devices can be provided by a gel or powder containing the capsid agents or by polymeric coating into which the capsid agents are suspended. Suitable polymeric materials for coatings or devices are those that are physiologically acceptable and through which a therapeutically effective amount of the capsid agent can diffuse. Suitable polymers include, but are not limited to, polyurethane, polymethacrylate, polyamide, polyester, polyethylene, polypropylene, polystyrene, polytetrafluoroethylene, polyvinyl-chloride, cellulose acetate, silicone elastomers, collagen, silk, etc. Such coatings are described, for instance, in U.S. Pat. No. 4,612,337, issued Sep. 16, 1986 to Fox et al. that is incorporated herein by reference in its entirety. The section below describes several methods to treat diseases or conditions associated with proliferation or migration of a cell that has a receptor that interacts with a parvovirus B19 capsid or fragment thereof (e.g., a P antigen containing cell), using a pharmaceutical having a capsid agent as an active ingredient.

Therapeutic and Prophylactic Approaches

In several aspects of the invention, capsid agents, in particular pharmaceuticals having capsid agents, are provided to a subject in need to treat or prevent a disease or condition associated with abnormal cell proliferation and/or cell migration. Methods to formulate pharmaceuticals for the inhibition of growth or migration of cells that have a receptor that interacts with a parvovirus B19 capsid or fragment thereof (e.g., a P antigen containing cell), including, but not limited to, hematopoietic cells and endothelial cells, are embodiments of the invention. That is, some embodiments include the use of medicaments comprising a capsid agent for the inhibition of growth and/or migration of cells that have a receptor that interacts with a parvovirus B19 capsid or fragment thereof (e.g., a P antigen containing cell), such as hematopoeitic cells and endothelial cells.

In one embodiment, for example, capsid agents can be used to inhibit hematopoesis in recipient subjects prior to in utero stem cell transplantation. In a previous study on tissue distribution of stem cells in the human fetus, it was estimated that a fetal transplantation with $5\times10^7$ cells in the second trimester would produce a donor-to-recipient ratio of approximately 1:1000–1:10000. Such a low ratio fails to provide transplanted cells with a competitive edge over the native stem cells. (Westgren et al., *Am J Obstet Gynecol,* 176:49 (1996)). To improve this ratio and the success of stem cell transplantation, capsid agents can be administered prior to transplantation so as to suppress the native stem cell population and thereby improve the transplantation. Furthermore, treatment of donor stem cells with anti-P monoclonal antibodies prior to transplantation can protect them from suppression by the capsid agents, and thereby provide an even more favorable status. Thus, one embodiment includes a medicament comprising a capsid agent for treatment of a patient prior to stem cell transplantation. This method of treatment can be performed by identifying a subject in need of an in utero stem cell transplantation and providing to said subject a therapeutically beneficial amount of a capsid agent that inhibits hematopoietic cell growth.

In a similar aspect of the invention, a method of non-myeloablative conditioning prior to postnatal stem cell transplantation is embodied. Recently, methods of nonmyeloblative conditioning have received considerable attention because such protocols are less toxic to the patients than the standard approach, which involves high-dose chemoradiotherapy. (Giralt et al., *Blood,* 89:4531 (1997); Slavin et al., *Blood,* 91:756 (1998)). However, complete donor hematopoietic chimerism using existing techniques in non-myeloablative therapy has not been very successful. By providing capsid agents prior to postnatal stem cell transplantation, the ratio of donor cells to recipient cells can be favorably skewed and donor hematopoietic chimerism can be achieved without radiation. Accordingly, a method of non-myeloablative conditioning can be performed by identifying a subject in need of non-myeloablative conditioning prior to postnatal stem cell transplantation and administering to said subject a therapeutically beneficial amount of a capsid agent.

Still another aspect of the invention is directed to a method of treating a subject suffering from an hematological proliferative disorders, e.g., Polycythemia Vera. Polycythemia Vera (PCV) is a haematological disease caused by an uncontrolled proliferation of red blood cells in the bone marrow. Cells of other lineage (leukocytes and thrombocytes) are involved in some patients and may also give rise to severe complications. The disease is normally seen in middle-aged and aged individuals (median age at diagnosis is 60 years) and the incidence in Sweden is 1.5 cases per 100,000 inhabitants. To date, there is no specific pharmacological treatment and current approaches to the problem seek to ease the symptoms of the slowly progressing disease. Median survival time without treatment is short. In younger individuals, with optimal treatment, one can obtain a reasonable quality of life for periods up to 20 years.

By administering capsid agents to subjects suffering from PCV, the proliferation of hematopoietic cells can be inhibited and an effective treatment for this deadly disease can be provided. Accordingly, a method of PCV can be performed by identifying a subject in need of treatment for PCV and administering to said subject a therapeutically beneficial amount of a capsid agent. Because a long-term treatment protocol is envisioned, preferably, the capsid agents used are ones that elicit a minimal immune response.

Yet another aspect of the invention is directed to a method of treating a patient for inhibition of endothelial cell growth. As described above, undesired endothelial cell growth can occur after surgical trauma, e.g., after the implantation of a valve, stent or other prosthetic or angioplasty, in said patient. Additionally, tumor development and metastasis requires endothelial cell growth and cell migration. Thus, embodiments of the invention concern medicaments that inhibit cancer, more specifically, angiogenesis and the cell migration events associated with metastasis.

Angiogenesis concerns the formation of new capillary blood vessels by a process of sprouting from pre-existing vessels. Angiogenesis occurs during development, as well as in a number of physiological and pathological settings, and is necessary for tissue growth, wound healing, female reproductive function, and is a component of pathological processes such as hemangioma formation and ocular neovascularization. However, much of the longstanding interest in angiogenesis comes from the discovery that solid tumors must undergo angiogenesis inorder to grow beyond a critical size. That is, tumors must recruit endothelial cells from the surrounding stroma to form their own endogenous microcirculation.

By administering capsid agents to subjects suffering from cancer, the proliferation and migration of endothelial cells can be inhibited and, thus, tumorigenesis and metastasis can be prevented. Accordingly, a method of inhibiting angiogenesis, tumorigenesis, or cancer can be performed by identifying a subject in need of an inhibition in angiogenesis, tumorigenesis, or cancer and administering to said subject a therapeutically beneficial amount of a capsid agent. Because a long-term treatment protocol is envisioned, preferably, the capsid agents used are ones that elicit a minimal immune response.

Additional embodiments of the invention include kits containing capsid agents, and written instructions for dosage and administration to a patient for hematopoietic progenitor cell growth inhibition, instructions for dosage and administration for hematopoietic progenitor cell growth inhibition in a patient prior to stem cell transplantation to said patient, such as a fetus, instructions for dosage and administration to a patient for endothelial cell growth inhibition and/or instructions for dosage and administration to a patient suffering from hematological proliferative disorders of P antigen positive cells, e.g., Polycythemia Vera.

Some kit embodiments also contain devices for letting blood (e.g., needles and syringe, finger prick lances, cappillary tube prick devices) and devices for low speed centrifugation of blood cells so as to enable a rapid determination of red blood cell hematocrit. By following red blood cell hematocrit, for example, one can rapidly determine the progress of treatment with the compositions described herein and one can adjust the dosage or type of medicament used in response to hematocrit levels.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A method of inhibiting hematopolesis comprising:

contacting a plurality of hematopoietic cells with an inhibiting amount of a B19 parvovirus capsid agent comprising the sequence glutamine-glutamine-tyrosine; and measuring the inhibition of hematopoiesis.

2. The method of claim 1 wherein the capsid agent comprises the VP1 and VP2 proteins.

3. The method of claim 1, wherein the capsid agent comprises the VP2 protein.

4. The method of claim 1, wherein the capsid agent comprises a sequence selected from the group consisting of SEQ. ID NO. 2, SEQ. ID. NO. 3, SEQ. ID. NO. 4, SEQ. ID. NO. 5, SEQ. ID. NO. 6, SEQ. ID. NO. 7, SEQ. ID. NO. 8, and SEQ. ID. NO. 48.

5. The method of claim 1, wherein the capsid agent consists of the sequence glutamine-glutamine-tyrosine.

6. The method of claim 4, wherein the sequence is SEQ. ID. NO. 2.

7. The method of claim 4, wherein the sequence is SEQ. ID. NO. 3.

8. The method of claim 4, wherein the sequence is SEQ. ID. NO. 4.

9. The method of claim 4, wherein the sequence is SEQ. ID. NO. 5.

10. The method of claim 4, wherein the sequence is SEQ. ID. NO. 6.

11. The method of claim 4, wherein the sequence is SEQ. ID. NO. 7.

12. The method of claim 4, wherein the sequence is SEQ. ID. NO. 8.

13. The method of claim 4, wherein the sequence is SEQ. ID. NO. 48.

14. The method of claim 1, wherein the capsid agent comprises the VP1 protein.

15. A method of inhibiting hematopoiesis comprising:

identifying a subject in need of an inhibition of hematopoiesis; and providing to said subject an inhibiting amount of a B19 parvovirus capsid agent comprising the sequence glutamine-glutamine-tyrosine.

16. The method of claim 15, wherein the capsid agent comprises the VP1 and VP2 proteins.

17. The method of claim 15, wherein the capsid agent comprises the VP2 protein.

18. The method of claim 15, wherein the capsid agent comprises a sequence selected from the group consisting of SEQ. ID. NO. 2, SEQ. ID. NO. 3, SEQ. ID. NO. 4, SEQ. ID. NO. 5, SEQ. ID. NO. 6, SEQ. ID. NO. 7, SEQ. ID. NO. 8, and SEQ. ID. NO. 48.

19. The method of claim 15, wherein the capsid agent consists of the sequence glutamine-glutamine-tyrosine.

20. The method of claim 15, wherein the sequence is SEQ. ID. NO. 2.

21. The method of claim 15, wherein the sequence is SEQ. ID. NO. 3.

22. The method of claim 15, wherein the sequence is SEQ. ID. NO. 4.

23. The method of claim 15, wherein the sequence is SEQ. ID. NO. 5.

24. The method of claim 15, wherein the sequence is SEQ. ID. NO. 6.

25. The method of claim 15, wherein the sequence is SEQ. ID. NO. 7.

26. The method of claim 15, wherein the sequence is SEQ. ID. NO. 8.

27. The method of claim 15, wherein the sequence is SEQ. ID. NO. 48.

28. The method of claim 15, wherein the subject has a hematological proliferative disorder.

29. The method of claim 28, wherein the hematological proliferative disorder is polycythemia vera.

* * * * *

UNITED STATES PATENT AND TRADEMARK OFFICE
CERTIFICATE OF CORRECTION

PATENT NO.    : 6,818,612 B2
DATED         : November 16, 2004
INVENTOR(S)   : Kristina Broliden et al.

It is certified that error appears in the above-identified patent and that said Letters Patent is hereby corrected as shown below:

<u>Title page,</u>
Item [56], References Cited, U.S. PATENT DOCUMENTS,
delete "538/17.4" and insert -- 536/17.4 --;
OTHER PUBLICATIONS,
"Gharakanian" reference, delete "Gharakanian" and insert -- Gharakhanian --;
"Chipman, et al;" reference, delete "ampty" and insert -- empty --.

<u>Column 61,</u>
Line 38, delete "hematopolesis" and insert -- hematopoiesis --.

Signed and Sealed this

Fourth Day of April, 2006

JON W. DUDAS
*Director of the United States Patent and Trademark Office*

SEQUENCE LISTING

```
<160> NUMBER OF SEQ ID NOS: 63

<210> SEQ ID NO 1
<211> LENGTH: 7
<212> TYPE: PRT
<213> ORGANISM: Artificial Sequence
<220> FEATURE:
<223> OTHER INFORMATION: Peptide fragments derived from parvovirus
      capsid particles

<400> SEQUENCE: 1

Lys Tyr Val Thr Gly Ile Asn
1               5

<210> SEQ ID NO 2
<211> LENGTH: 21
<212> TYPE: PRT
<213> ORGANISM: Artificial Sequence
<220> FEATURE:
<223> OTHER INFORMATION: Peptide fragments derived from parvovirus
      capsid particles

<400> SEQUENCE: 2

Gly Leu Asn Met His Thr Tyr Phe Pro Asn Lys Gly Thr Gln Gln Tyr
1               5                   10                  15

Thr Asp Gln Ile Glu
            20

<210> SEQ ID NO 3
<211> LENGTH: 16
<212> TYPE: PRT
<213> ORGANISM: Artificial Sequence
<220> FEATURE:
<223> OTHER INFORMATION: Peptide fragments derived from parvovirus
      capsid particles

<400> SEQUENCE: 3

Thr Tyr Phe Pro Asn Lys Gly Thr Gln Gln Tyr Thr Asp Gln Ile Glu
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: Peptide fragments derived from parvovirus
      capsid particles

<400> SEQUENCE: 4

Asn Lys Gly Thr Gln Gln Tyr Thr Asp Gln Ile Glu
1               5                   10
```

-continued

```
<210> SEQ ID NO 5
<211> LENGTH: 10
<212> TYPE: PRT
<213> ORGANISM: Artificial Sequence
<220> FEATURE:
<223> OTHER INFORMATION: Peptide fragments derived from parvovirus
      capsid particles

<400> SEQUENCE: 5

Asn Lys Gly Thr Gln Gln Tyr Thr Asp Gln
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Peptide fragments derived from parvovirus
      capsid particles

<400> SEQUENCE: 6

Asn Lys Gly Thr Gln Gln Tyr Thr
1               5

<210> SEQ ID NO 7
<211> LENGTH: 6
<212> TYPE: PRT
<213> ORGANISM: Artificial Sequence
<220> FEATURE:
<223> OTHER INFORMATION: Peptide fragments derived from parvovirus
      capsid particles

<400> SEQUENCE: 7

Gln Gln Tyr Thr Asp Gln
1               5

<210> SEQ ID NO 8
<211> LENGTH: 4
<212> TYPE: PRT
<213> ORGANISM: Artificial Sequence
<220> FEATURE:
<223> OTHER INFORMATION: Peptide fragments derived from parvovirus
      capsid particles

<400> SEQUENCE: 8

Gln Gln Tyr Gln
1

<210> SEQ ID NO 9
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 9

Met Thr Ser Val Asn Ser Ala Glu Ala Ser Thr Gly Ala Gly Gly
1               5                   10                  15

Gly Ser Asn Pro
            20

<210> SEQ ID NO 10
<211> LENGTH: 20
<212> TYPE: PRT
<213> ORGANISM: Artificial Sequence
<220> FEATURE:
<223> OTHER INFORMATION: Peptide fragments derived from parvovirus
``` capsid

<400> SEQUENCE: 10

Thr Gly Ala Gly Gly Gly Gly Ser Asn Pro Val Lys Ser Met Trp Ser
1               5                   10                  15

Glu Gly Ala Thr
            20

<210> SEQ ID NO 11
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 11

Val Lys Ser Met Trp Ser Glu Gly Ala Thr Phe Ser Ala Asn Ser Val
1               5                   10                  15

Thr Cys Thr Phe
            20

<210> SEQ ID NO 12
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 12

Phe Ser Ala Asn Ser Val Thr Cys Thr Phe Ser Arg Gln Phe Leu Ile
1               5                   10                  15

Pro Tyr Asp Pro
            20

<210> SEQ ID NO 13
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 13

Ser Arg Gln Phe Leu Ile Pro Tyr Asp Pro Glu His His Tyr Lys Val
1               5                   10                  15

Phe Ser Pro Ala
            20

<210> SEQ ID NO 14
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 14

Glu His His Tyr Lys Val Phe Ser Pro Ala Ala Ser Ser Cys His Asn
1               5                   10                  15

Ala Ser Gly Lys
            20

<210> SEQ ID NO 15
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 15

Ala Ser Ser Cys His Asn Ala Ser Gly Lys Glu Ala Lys Val Cys Thr
 1               5                  10                  15
Ile Ser Pro Ile
            20

<210> SEQ ID NO 16
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 16

Glu Ala Lys Val Cys Thr Ile Ser Pro Ile Met Gly Tyr Ser Thr Pro
 1               5                  10                  15
Trp Arg Tyr Leu
            20

<210> SEQ ID NO 17
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 17

Met Gly Tyr Ser Thr Pro Trp Arg Tyr Leu Asp Phe Asn Ala Leu Asn
 1               5                  10                  15
Leu Phe Phe Ser
            20

<210> SEQ ID NO 18
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 18

Asp Phe Asn Ala Leu Asn Leu Phe Phe Ser Pro Leu Glu Phe Gln His
 1               5                  10                  15
Leu Ile Glu Asn
            20

<210> SEQ ID NO 19
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 19

Pro Leu Glu Phe Gln His Leu Ile Glu Asn Tyr Gly Ser Ile Ala Pro

```
                 1               5              10             15

Asp Ala Leu Thr
            20

<210> SEQ ID NO 20
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 20

Tyr Gly Ser Ile Ala Pro Asp Ala Leu Thr Val Thr Ile Ser Glu Ile
 1               5                  10                  15

Ala Val Lys Asp
            20

<210> SEQ ID NO 21
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 21

Val Thr Ile Ser Glu Ile Ala Val Lys Asp Val Thr Asp Lys Thr Gly
 1               5                  10                  15

Gly Gly Val Gln
            20

<210> SEQ ID NO 22
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 22

Val Thr Asp Lys Thr Gly Gly Gly Val Gln Val Thr Asp Ser Thr Thr
 1               5                  10                  15

Gly Arg Leu Cys
            20

<210> SEQ ID NO 23
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 23

Val Thr Asp Ser Thr Thr Gly Arg Leu Cys Met Leu Val Asp His Glu
 1               5                  10                  15

Tyr Lys Tyr Pro
            20

<210> SEQ ID NO 24
<211> LENGTH: 20
<212> TYPE: PRT
<213> ORGANISM: Artificial Sequence
<220> FEATURE:
```

```
-continued

<223> OTHER INFORMATION: Peptide fragments derived from parvovirus
      capsid

<400> SEQUENCE: 24

Met Leu Val Asp His Glu Tyr Lys Tyr Pro Tyr Val Leu Gly Gln Gly
 1               5                  10                  15

Gln Asp Thr Leu
            20

<210> SEQ ID NO 25
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 25

Tyr Val Leu Gly Gln Gly Gln Asp Thr Leu Ala Pro Glu Leu Pro Ile
 1               5                  10                  15

Trp Val Tyr Phe
            20

<210> SEQ ID NO 26
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 26

Ala Pro Glu Leu Pro Ile Trp Val Tyr Phe Pro Pro Gln Tyr Ala Tyr
 1               5                  10                  15

Leu Thr Val Gly
            20

<210> SEQ ID NO 27
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 27

Pro Pro Gln Tyr Ala Tyr Leu Thr Val Gly Asp Val Asn Thr Gln Gly
 1               5                  10                  15

Ile Ser Gly Asp
            20

<210> SEQ ID NO 28
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 28

Asp Val Asn Thr Gln Gly Ile Ser Gly Asp Ser Lys Lys Leu Ala Ser
 1               5                  10                  15

Glu Glu Ser Ala
            20
```

```
<210> SEQ ID NO 29
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 29

Ser Lys Lys Leu Ala Ser Glu Glu Ser Ala Phe Tyr Val Leu Glu His
1               5                   10                  15

Ser Ser Phe Gln
            20

<210> SEQ ID NO 30
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 30

Phe Tyr Val Leu Glu His Ser Ser Phe Gln Leu Leu Gly Thr Gly Gly
1               5                   10                  15

Thr Ala Thr Met
            20

<210> SEQ ID NO 31
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 31

Leu Leu Gly Thr Gly Gly Thr Ala Thr Met Ser Tyr Lys Phe Pro Pro
1               5                   10                  15

Val Pro Pro Glu
            20

<210> SEQ ID NO 32
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 32

Ser Tyr Lys Phe Pro Pro Val Pro Pro Glu Asn Leu Glu Gly Cys Ser
1               5                   10                  15

Gln His Phe Tyr
            20

<210> SEQ ID NO 33
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 33
```

-continued

```
Asn Leu Glu Gly Cys Ser Gln His Phe Tyr Glu Met Tyr Asn Pro Leu
 1               5                  10                  15

Tyr Gly Ser Arg
            20

<210> SEQ ID NO 34
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 34

Glu Met Tyr Asn Pro Leu Tyr Gly Ser Arg Leu Gly Val Pro Asp Thr
 1               5                  10                  15

Leu Gly Gly Asp
            20

<210> SEQ ID NO 35
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 35

Leu Gly Val Pro Asp Thr Leu Gly Gly Asp Pro Lys Phe Arg Ser Leu
 1               5                  10                  15

Thr His Glu Asp
            20

<210> SEQ ID NO 36
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 36

Pro Lys Phe Arg Ser Leu Thr His Glu Asp His Ala Ile Gln Pro Gln
 1               5                  10                  15

Asn Phe Met Pro
            20

<210> SEQ ID NO 37
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 37

His Ala Ile Gln Pro Gln Asn Phe Met Pro Gly Pro Leu Val Asn Ser
 1               5                  10                  15

Val Ser Thr Lys
            20

<210> SEQ ID NO 38
<211> LENGTH: 20
<212> TYPE: PRT
<213> ORGANISM: Artificial Sequence
```

```
<220> FEATURE:
<223> OTHER INFORMATION: Peptide fragments derived from parvovirus
      capsid

<400> SEQUENCE: 38

Gly Pro Leu Val Asn Ser Val Ser Thr Lys Glu Gly Asp Ser Ser Asn
  1               5                  10                  15

Thr Gly Ala Gly
            20

<210> SEQ ID NO 39
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 39

Glu Gly Asp Ser Ser Asn Thr Gly Ala Gly Lys Ala Leu Thr Gly Leu
  1               5                  10                  15

Ser Thr Gly Thr
            20

<210> SEQ ID NO 40
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 40

Lys Ala Leu Thr Gly Leu Ser Thr Gly Thr Ser Gln Asn Thr Arg Ile
  1               5                  10                  15

Ser Leu Arg Pro
            20

<210> SEQ ID NO 41
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 41

Ser Gln Asn Thr Arg Ile Ser Leu Arg Pro Gly Pro Val Ser Gln Pro
  1               5                  10                  15

Tyr His His Trp
            20

<210> SEQ ID NO 42
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 42

Gly Pro Val Ser Gln Pro Tyr His His Trp Asp Thr Asp Lys Tyr Val
  1               5                  10                  15

Thr Gly Ile Asn
            20
```

```
<210> SEQ ID NO 43
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 43

Asp Thr Asp Lys Tyr Val Thr Gly Ile Asn Ala Ile Ser His Gly Gln
 1               5                  10                  15

Thr Thr Tyr Gly
            20

<210> SEQ ID NO 44
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 44

Ala Ile Ser His Gly Gln Thr Thr Tyr Gly Asn Ala Glu Asp Lys Glu
 1               5                  10                  15

Tyr Gln Gln Gly
            20

<210> SEQ ID NO 45
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 45

Asn Ala Glu Asp Lys Glu Tyr Gln Gln Gly Val Gly Arg Phe Pro Asn
 1               5                  10                  15

Glu Lys Glu Gln
            20

<210> SEQ ID NO 46
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 46

Val Gly Arg Phe Pro Asn Glu Lys Glu Gln Leu Lys Gln Leu Gln Gly
 1               5                  10                  15

Leu Asn Met His
            20

<210> SEQ ID NO 47
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 47
```

Leu Lys Gln Leu Gln Gly Leu Asn Met His Thr Tyr Phe Pro Asn Lys
1               5                   10                  15

Gly Thr Gln Gln
            20

<210> SEQ ID NO 48
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 48

Thr Tyr Phe Pro Asn Lys Gly Thr Gln Gln Tyr Thr Asp Gln Ile Glu
1               5                   10                  15

Arg Pro Leu Met
            20

<210> SEQ ID NO 49
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 49

Tyr Thr Asp Gln Ile Glu Arg Pro Leu Met Val Gly Ser Val Trp Asn
1               5                   10                  15

Arg Arg Ala Leu
            20

<210> SEQ ID NO 50
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 50

Val Gly Ser Val Trp Asn Arg Arg Ala Leu His Tyr Glu Ser Gln Leu
1               5                   10                  15

Trp Ser Lys Ile
            20

<210> SEQ ID NO 51
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 51

His Tyr Glu Ser Gln Leu Trp Ser Lys Ile Pro Asn Leu Asp Asp Ser
1               5                   10                  15

Phe Lys Thr Gln
            20

<210> SEQ ID NO 52
<211> LENGTH: 20
<212> TYPE: PRT

```
<213> ORGANISM: Artificial Sequence
<220> FEATURE:
<223> OTHER INFORMATION: Peptide fragments derived from parvovirus
      capsid

<400> SEQUENCE: 52

Pro Asn Leu Asp Asp Ser Phe Lys Thr Gln Phe Ala Ala Leu Gly Gly
1               5                   10                  15

Trp Gly Leu His
            20

<210> SEQ ID NO 53
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 53

Phe Ala Ala Leu Gly Gly Trp Gly Leu His Gln Pro Pro Pro Gln Ile
1               5                   10                  15

Phe Leu Lys Ile
            20

<210> SEQ ID NO 54
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 54

Gln Pro Pro Pro Gln Ile Phe Leu Lys Ile Leu Pro Gln Ser Gly Pro
1               5                   10                  15

Ile Gly Gly Ile
            20

<210> SEQ ID NO 55
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 55

Leu Pro Gln Ser Gly Pro Ile Gly Gly Ile Lys Ser Met Gly Ile Thr
1               5                   10                  15

Thr Leu Val Gln
            20

<210> SEQ ID NO 56
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 56

Lys Ser Met Gly Ile Thr Thr Leu Val Gln Tyr Ala Val Gly Ile Met
1               5                   10                  15

Thr Val Thr Met
```

20

<210> SEQ ID NO 57
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 57

Tyr Ala Val Gly Ile Met Thr Val Thr Met Thr Phe Lys Leu Gly Pro
 1               5                  10                  15

Arg Lys Ala Thr
            20

<210> SEQ ID NO 58
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 58

Thr Phe Lys Leu Gly Pro Arg Lys Ala Thr Gly Arg Trp Asn Pro Gln
 1               5                  10                  15

Pro Gly Val Tyr
            20

<210> SEQ ID NO 59
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 59

Gly Arg Trp Asn Pro Gln Pro Gly Val Tyr Pro Pro His Ala Ala Gly
 1               5                  10                  15

His Leu Pro Tyr
            20

<210> SEQ ID NO 60
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 60

Pro Pro His Ala Ala Gly His Leu Pro Tyr Val Leu Tyr Asp Pro Thr
 1               5                  10                  15

Ala Thr Asp Ala
            20

<210> SEQ ID NO 61
<211> LENGTH: 20
<212> TYPE: PRT
<213> ORGANISM: Artificial Sequence
<220> FEATURE:
<223> OTHER INFORMATION: Peptide fragments derived from parvovirus
      capsid -continued

```
<400> SEQUENCE: 61

Val Leu Tyr Asp Pro Thr Ala Thr Asp Ala Lys Gln His His Arg His
 1              5                   10                  15

Gly Tyr Glu Lys
            20

<210> SEQ ID NO 62
<211> LENGTH: 20
<212> TYPE: PRT
<213> ORGANISM: Artificial Sequence
<220> FEATURE:
<223> OTHER INFORMATION: Peptide fragments derived from parvovirus
      capsid

<400> SEQUENCE: 62

Lys Gln His His Arg His Gly Tyr Glu Lys Pro Glu Glu Leu Trp Thr
 1              5                   10                  15

Ala Lys Ser Arg
            20

<210> SEQ ID NO 63
<211> LENGTH: 14
<212> TYPE: PRT
<213> ORGANISM: Artificial Sequence
<220> FEATURE:
<223> OTHER INFORMATION: Peptide fragments derived from parvovirus
      capsid

<400> SEQUENCE: 63

Pro Glu Glu Leu Trp Thr Ala Lys Ser Arg Val His Pro Leu
 1              5                   10
```